US009023916B2

(12) United States Patent
Blömker et al.

(10) Patent No.: US 9,023,916 B2
(45) Date of Patent: May 5, 2015

(54) COMPOSITE MATERIAL COMPRISING A MONOMER WITH A POLYALICYCLIC STRUCTURE ELEMENT

(75) Inventors: Tobias Blömker, Cuxhaven (DE); Manfred Stepputtis, Kutenholz (DE); Reinhard Maletz, Cuxhaven (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 790 days.

(21) Appl. No.: 13/248,650

(22) Filed: Sep. 29, 2011

(65) Prior Publication Data

US 2012/0082958 A1  Apr. 5, 2012

(30) Foreign Application Priority Data

Sep. 30, 2010  (DE) .................. 10 2010 041 783
Sep. 29, 2011  (EP) ..................... 11183328

(51) Int. Cl.
*A61K 6/083* (2006.01)
*A61K 6/027* (2006.01)
A61K 6/00 (2006.01)
A61L 27/44 (2006.01)

(52) U.S. Cl.
CPC ............. *A61K 6/0276* (2013.01); *A61K 6/0073* (2013.01); *A61K 6/0091* (2013.01); *A61L 27/446* (2013.01)

(58) Field of Classification Search
CPC ....... A61K 6/08; A61K 6/083; A61K 6/0276; A61K 6/0091; A61K 6/0073; A61K 6/0008; A61K 27/4446
USPC ........................................................ 523/115
See application file for complete search history.

(56) References Cited

U.S. PATENT DOCUMENTS

| | | | |
|---|---|---|---|
| 4,002,669 A | 1/1977 | Gross et al. | |
| 4,160,080 A | 7/1979 | Koenig et al. | |
| 4,323,696 A | 4/1982 | Schmitz-Josten et al. | |
| 4,447,520 A | 5/1984 | Henne et al. | |
| 4,772,530 A | 9/1988 | Gottschalk et al. | |
| 4,874,450 A | 10/1989 | Gottschalk | |
| 4,925,982 A | 5/1990 | Urano et al. | |
| 4,954,414 A | 9/1990 | Adair et al. | |
| 5,055,372 A | 10/1991 | Shanklin et al. | |
| 5,057,393 A | 10/1991 | Shanklin et al. | |
| 5,063,257 A | 11/1991 | Akahane et al. | |
| 5,761,169 A | 6/1998 | Mine et al. | |
| 5,936,006 A * | 8/1999 | Rheinberger et al. | 523/116 |
| 6,399,037 B1 | 6/2002 | Pflug et al. | |
| 6,670,499 B1 | 12/2003 | Inoue et al. | |
| 7,081,485 B2 | 7/2006 | Suh et al. | |
| 7,148,382 B2 | 12/2006 | Wolf et al. | |
| 7,381,785 B2 | 6/2008 | Detrembleur et al. | |
| 7,601,767 B2 * | 10/2009 | Ruppert et al. | 523/116 |
| 2007/0027229 A1 | 2/2007 | Moszner et al. | |
| 2009/0036565 A1 * | 2/2009 | Utterodt et al. | 523/116 |

FOREIGN PATENT DOCUMENTS

| | | |
|---|---|---|
| DE | 2200021 | 7/1973 |
| DE | 2419887 | 11/1974 |
| DE | 3236026 A1 | 3/1984 |
| DE | 3338077 A1 | 5/1985 |
| DE | 3703120 A1 | 1/1988 |
| DE | 3707908 A1 | 3/1988 |
| DE | 4231579 A1 | 3/1993 |
| DE | 4416857 C1 | 6/1995 |
| DE | 19701599 A1 | 7/1998 |
| DE | 19903177 A1 | 7/2000 |
| DE | 10119831 A1 | 10/2002 |
| DE | 10352260 B3 | 4/2005 |
| DE | 102004060285 A1 | 6/2006 |
| DE | 60116142 T2 | 7/2006 |
| DE | 102006019092 A1 | 3/2007 |
| DE | 102005053775 A1 | 5/2007 |
| DE | 60216951 T2 | 6/2007 |
| DE | 102006050153 A1 | 5/2008 |
| DE | 102006060983 A1 | 6/2008 |
| DE | 102007034457 A1 | 1/2009 |
| DE | 19617931 C5 * | 7/2010 |
| EP | 0057474 A2 | 7/1979 |
| EP | 0007508 A2 | 2/1980 |
| EP | 0023685 A2 | 7/1980 |
| EP | 0047902 A2 | 8/1981 |
| EP | 0049631 A1 | 10/1981 |
| EP | 0059451 A1 | 2/1982 |
| EP | 0173567 A2 | 8/1985 |
| EP | 0184095 A2 | 11/1985 |
| EP | 0206074 A2 | 6/1986 |
| EP | 0209700 A2 | 6/1986 |
| EP | 0264551 A2 | 7/1987 |
| EP | 0254950 A2 | 2/1988 |
| EP | 0325266 A2 | 7/1989 |
| EP | 0262629 F2 | 9/1989 |
| EP | 0366977 A2 | 10/1989 |
| EP | 0345581 A2 | 12/1989 |
| EP | 0682012 A1 | 4/1995 |
| EP | 0712840 A1 | 5/1996 |
| EP | 0783880 A2 | 7/1997 |
| EP | 0948955 A1 | 4/1998 |
| EP | 0867457 A1 | 9/1998 |
| EP | 0980682 A1 | 8/1999 |
| EP | 1112995 B1 | 9/1999 |
| EP | 1563821 A1 | 1/2001 |
| EP | 1236459 B1 | 7/2001 |
| EP | 1238993 A1 | 9/2002 |
| EP | 1645582 A1 | 4/2006 |

(Continued)

*Primary Examiner* — Michael Pepitone
(74) *Attorney, Agent, or Firm* — Duane Morris LLP; J. Rodman Steele, Jr.; Gregory M. Lefkowitz

(57) ABSTRACT

A composite material and method of making and using the same is described. In particular a dental (and preferably photocurable) composite material, and the use of a composite material according to the invention as a dental material and a method for preparation of a composite material according to the invention. Also disclosed are novel radically polymerizable monomers comprising at least one polyalicyclic structure element and certain ethylenic structure elements, which are particularly suitable for use in a composite material according to the invention.

23 Claims, No Drawings

(56) References Cited

FOREIGN PATENT DOCUMENTS

| | | |
|---|---|---|
| EP | 1719497 A1 | 11/2006 |
| EP | 1720506 A1 | 11/2006 |
| EP | 1839640 A2 | 3/2007 |
| EP | 1935393 A2 | 6/2008 |
| EP | 2016931 A2 | 1/2009 |
| EP | 2031003 A1 | 3/2009 |
| EP | 2031005 A2 | 3/2009 |
| GB | 1110673 | 4/1968 |
| GB | 1576080 | 10/1980 |
| GB | 2310855 A | 9/1997 |
| JP | 11-21370 A | 5/1989 |
| JP | 7-206740 | 8/1995 |
| JP | 7-206741 A | 8/1995 |
| WO | 0144873 A1 | 8/2001 |
| WO | 02092021 A1 | 11/2002 |
| WO | 02092023 A1 | 11/2002 |
| WO | 03035013 A1 | 5/2003 |
| WO | 2006063891 A1 | 6/2006 |
| WO | 2009065873 A2 | 5/2009 |

* cited by examiner

COMPOSITE MATERIAL COMPRISING A MONOMER WITH A POLYALICYCLIC STRUCTURE ELEMENT

CROSS-REFERENCE TO RELATED APPLICATIONS

This application claims priority to German Application No. DE 10 2010 041 783.1, filed Sep. 30, 2010 and European Application No. EP 11183328, filed Sep. 29, 2011, the entireties of which are incorporated herein by reference.

FIELD OF THE INVENTION

The present invention relates to a composite material, particularly a dental (and in particular photocurable) composite material, and the use of a composite material according to the invention as a dental material and a method for preparing a composite material according to the invention. The invention further relates to novel radically polymerizable monomers comprising at least one polyalicyclic structure element and certain ethylenic structure elements, which are particularly suitable for use in a composite material according to the invention, in particular a dental composite material according to the invention, and their use in a composite material.

BACKGROUND OF THE INVENTION

Over the last 50 years amalgam, which for more than a century was dominant in dental filling treatment, has to an increasing extent been replaced by synthetic-based composite materials. The reasons for this change were firstly a desire by patients for aesthetic dental treatment in the side teeth area as well and secondly developments in dental restoration synthetics. In particular synthetic filling materials with 2,2-bis[4-(2-hydroxy-3-methacryloyl-oxypropoxy)phenyl)propane (Bis-GMA) as the base substances have been developed.

Bis-GMA, synthesized from 2 mol glycidyl methacrylate and one mol bipshenol A, contains at both its ends a terminal vinyl group which polymerizes quickly in a radical reaction and results in a cross-linked polymer. The chemical structure of Bis-GMA has a number of special features:

The two aromatic rings of the bisphenol A structure element, which bond with the propane radical are sterically impeded in their rotation. Quantum chemical calculations and experimental research show that the hydrogen atoms at positions 2 and 6 of each aromatic ring overlap with the hydrogen atoms of the two methyl groups of the propane radical, so that even at high temperatures no rotation of the aromatic rings is possible. The molecule thus has the most rigid possible conformation, which results in a comparatively high modulus of elasticity.

The molecule has both free hydroxyl groups and carbonyl oxygen atoms. The presence of these structure elements allows interactions and the development of hydrogen bridge bonds between neighboring Bis-GMA molecules.

These structural characteristics of the Bis-GMA allow the development of a so-called superstructure based on hydrogen bridge bonds in the polymer, wherein the superstructures because of the rigid monomer conformation are packed extremely densely. This leads to particularly good mechanical characteristics of the material. In addition, the superstructures and the extraordinarily dense packing of the molecular chains ensure that the absorption of water from the oral cavity into the dental material is made considerably harder. Absorption of water leads to a softening of the material and can trigger a hydrolytic decomposition of the ester function of the polymer.

Because of its size and distinctly rigid conformation it is also unlikely that unreacted Bis-GMA, should it leak from the cross-linked polymer, will reach the pulp via the dentinal tubules. Bis-GMA would likewise not be expected to easily pass through biological membranes and bioaccumulate. For these reasons a low toxicity and a generally good biocompatibility is attributed to the Bis-GMA. However, the toxicological characteristics of Bisphenol-A, the starting product for the synthesis of the Bis-GMA, which in traces is always contained in Bis-GMA, have not yet been conclusively clarified.

The molecules of the Bis-GMA, because of their size, are highly space-filling. During the cross-linking therefore the polymerization shrinkage is typically low, for during the radical polymerization of equal substance quantities of Bis-GMA and for example methacrylate fewer bonds are formed than with methyl methacrylate, and thus less bond energy is released.

As a phenomenon, the polymerization shrinkage corresponds to a change in the density occurring during and after cross-linking. This substantially has two causes. On the one hand during polymerization, it is a case of the approximation of the monomeric building blocks of a van der Waals gap to the gap of a covalent bond, and on the other the packing density of the polymer chains is higher than the packing density of the monomers. The shrinkage (in volume) of the reaction resin mass substantially depends on the number of functional groups that have been reacted. The shrinkage takes place both in the fluid state, thus at the very start of the polymerization, as well as during and after gelling. Overall shrinkage comprises a physical and chemical component. While the physical shrinkage is directionally determined and occurs spatially from the outer areas of the polymer, as the temperature drops, internally towards the centre of the molding material, the chemical component is not directionally determined and results solely from the polymer formation. At the start of the polymerization the volume shrinkage can be compensated by the backflow of the material. But within a short time the polymer network has developed so extensively that the gel point is reached, the mobility of the monomers is restricted and backflow of the material is impossible. In this state disadvantageous stresses occur within the material, which when it is used as a dental material lead either to it coming loose from the cavity walls and thus to the formation of marginal gaps or which weaken the material through the formation of volume defects.

In order to counteract the shrinkage, apart from the use of more voluminous monomers such as the Bis-GMA discussed above, the dental composition frequently has volume-stable fillers added. This results in a drop in the number of cross-linkable groups and so the shrinkage and the thermal energy released during bond formation are reduced. Both the use of particularly space-filling monomers and the addition of fillers, however, disadvantageously lead to an increase in the viscosity and thus to a reduction in processability. Therefore conventional dental composite materials contain so-called low molecular reactive thinners, which lower the viscosity thus ensuring the processability of the composite material. Conventional dental composite materials thus consist of a voluminous monomer such as in particular Bis-GMA and low-molecular monomers (reactive thinners) such as for example triethylene glycol dimethacrylate (TEDMA) as well as normal fillers, polymerization initiators and additives.

Through low-molecular monomers (reactive thinners) such as for example triethylene glycol dimethacrylate certain mechanical characteristics of the material are improved, since these molecules even after reaching the gel point are still so mobile that they find reaction partners and through the bonds formed increase the network density of the polymer. TEDMA and other low-molecular monomers of similar structure are as a rule, however, also highly flexible, since these molecules are able to rotate around their ether bonds unhindered. Due to their flexible nature the low-molecular monomers disrupt the homogeneity of the rigid and closely packed Bis-GMA structures, so that apart from some mechanical characteristics being improved others are adversely affected. Therefore to date it has not been possible to indicate Bis-GMA composite materials with minimal polymerization shrinkage and overall good mechanical characteristics, in particular a good abrasion resistance and surface hardness of the cured composite material.

In the past monomer systems have been proposed in which via ring opening reactions the volume contraction is balanced out. Other developments use a cationic ring opening polymerization instead of a radical addition polymerization. Furthermore, liquid crystal monomers, dendritic monomers or organic-inorganic hybrid materials, such as ormocers (organically modified ceramics) have been tested. The conceptual aim is to overcome the volume shrinkage by shifting the balance between broken and newly formed covalent bonds or by differentiation in the packing density between the liquid phase and solid phase.

Also already known is the use of radically polymerizable methacrylic acid or acrylic acid esters with a tricyclo [$5.2.1.0^{2,6}$]-decane (TCD) structure element for the preparation of low shrinkage dental materials. Because of their rigid three-ring conformation and complete steric restriction of mobility, this group of substances is similar to Bis-GMA. In addition, the central aliphatic hydrocarbon element brings about the creation of a considerable hydrophobia, which results in a high water resistance of the polymer. Radically polymerizable methacrylic acid or acrylic acid esters with a tricyclo[$5.2.1.0^{2,6}$]-decane structure element have a very low viscosity and are thus easy to process, and their refractive index also suits the glass ceramic normally used in dental materials.

Dental composite materials containing radically polymerizable methacrylic acid or acrylic acid esters with a tricyclo [$5.2.1.0^{2,6}$]-decane structure element are, inter alia, mentioned in the following printed publications: DE 28 16 823 A1, DE 24 19 887 A1, DE 24 06 557 A1, DE 29 31 926 A1, DE 35 22 005 A1, DE 35 22 006 A1, DE 37 03 080 A1, DE 37 03 130 A1, DE 37 07 908 A1, DE 38 19 777 A1, DE 197 01 599 A1 and DE 699 35 794 T2.

Documents DE 22 00 021 A1, EP 0 023 686 A2, EP 0 049 631 A1, JP 7-206740 A, JP 7-206741 A and JP 11-21370 A likewise disclose radically polymerizable methacrylic acid or acrylic acid esters with a tricyclo[$5.2.1.0^{2,6}$]-decane structure element.

DE 10 2005 021 332 B4 describes composite materials that are claimed to have low shrink force. The composite material disclosed with a total filler content of 80 through 95 wt. % contains
  in the filler component
    0.5 through 10 wt. % of non-agglomerated nanofillers with particle sizes of 1 nm through 50 nm,
  and
    at least 60 wt. % of a filler blend of 50 through 90 wt. % of coarse and 10 through 50 wt. % fine particle dental glasses, having a size ratio, with reference to the average particle size of fine particles to coarse particles of 1:4 through 1:30, wherein the proportion of fine particle dental glasses is claimed to be a maximum of 40 wt. % of the filler mixture,
  and as monomer component a mixture of
    60-80 wt. % Bis-GMA or TCD-di-HEMA (bis(methacryloyloxymethyl-)-tricyclo[$5.2.1.0^{2,6}$]decane) or TCD-di-HEA (bis(acryloyloxymethyl)tricyclo[$5.2.1.0^{2,6}$]decane)
    10-18 wt. % UDMA (urethane dimethacrylate)
    radical TEDMA and/or multifunctional cross-linkers
  up to 1 wt. % initiator(s).

By the use of non-agglomerated nanofillers and a filler blend of coarse and fine particle dental glasses, through the extensive substitution of TEDMA by UDMA and the optional use of radically polymerizable methacrylic acid or acrylic acid esters with a tricyclo[$5.2.1.0^{2,6}$]-decane structure element and the optional reduction of the initiator quantity according to DE 10 2005 021 332 B4 the achievement of a reduction in the polymerization shrinkage is claimed. This is demonstrated only for TCD-free compositions, however.

In DE 10 2005 053 775 A1 a self-curing or dual-curing, fine-flowing composite material for preparation of a dental liner with polymerization in two stages with two bonding times and delayed polymerization characteristic, which is envisaged for use in the area of the cavity wall in a thin coating, is disclosed. Preferred monomer components include TCD-di-HEMA and TCD-di-HEA.

EP 1 935 393 A2 and DE 10 2006 060 983 A1 relate to dental composites comprising radically polymerizable acrylic acid esters with a tricyclo[$5.2.1.0^{2,6}$]-decane structure element. The higher degree of polymerization of these is claimed to be advantageous for the mechanical characteristics of the composites. However, acrylate monomers are considered unsuitable for dental applications because of their harmful toxicological characteristics. Following curing the cross-linked TCD acrylate monomers are nevertheless claimed to have a very favorable biocompatibility. This document also describes compositions which substantially are Bis-GMA-free.

EP 2 016 931 A2 and DE 10 2007 034 457 A1 also described dental composites comprising radically polymerizable methacrylic acid or acrylic acid esters with a tricyclo [$5.2.1.0^{2,6}$]-decane structure element, wherein the monomer components must contain both Bis-GMA and TCD-di-HEMA or TCD-di-HEA.

WO 03/035013 A1 and DE 602 16 951 T2 relate to dental adhesive compositions for binding of dental restoration means to dentin and/or tooth enamel. In these documents inter alia the preparation of 3,(4),8,(9)-bis(2-propanamidomethyl) tricyclo[$5.2.1.0$]$^{2,6}$-decane is described.

DESCRIPTION OF THE INVENTION

From the prior art, therefore, compositions are known based on radically polymerizable methacrylic acid or acrylic acid esters with a tricyclo[$5.2.1.0^{2,6}$]-decane structure element, which lead to low-shrinkage dental composite materials. However, with these compositions no composite materials are obtainable which simultaneously are low shrinkage and meet high mechanical requirements, in particular in relation to the abrasion resistance and surface hardness of the polymer. The primary object for the present invention was thus to provide a dental composite material, which has both low shrinkage and a high abrasion resistance and surface hardness.

Further objects arise from the following description and the attached claims.

The primary object is achieved by a composite material according to the invention, in particular a dental composite material according to the invention consisting of or comprising
(a) >75 (preferably 80) through 95 wt. %, in relation to the total weight of the composite material, of a mixture of fillers comprising
  (a1) >10 (preferably >11, particularly preferably >12) through 30 wt. % non-agglomerated, organically surface-modified nanoparticles with an average particle size of less than 200 nm (preferably less than 100 nm, particularly preferably less than 60 nm)
  and
  (a2) 45 through <85 wt. % (preferably <84, particularly preferably <83 wt. %) of microparticles with an average particle size of 0.4 µm through 10 µm and
(a3) optionally other fillers,
wherein the weight percentages given for components (a1) and (a2) relate to the total weight of the composite material,
(b) 3 through <25 (preferably up to 20) wt. %, in relation to the total weight of the composite material, of a mixture of monomers comprising
(b1) one, two or a plurality of monomers selected from the group consisting of compounds (monomers) with the structure $Q(YZ_e)_b$, wherein the following applies:
Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $YZ_e$ are substituted by alkyl groups (here preferably C1-C4-alkyl), alkoxy groups (here preferably C1-C4-alkoxy), halogen atoms (here preferably F) or trifluormethyl groups;
b is an integer selected from the group of integers 1, 2, 3 and 4;
each Z represents a structure element, which independently of any further structure elements Z is selected from the group consisting of

—O—(C=O)—CH=CH$_2$,—O—(C=O)—C(CH$_3$)=CH$_2$,

—(C=O)—CH=CH$_2$,—(C=O)—C(CH$_3$)=CH$_2$,

—CH=CH$_2$,—C(CH$_3$)=CH$_2$ and —O—CH=CH$_2$, each index e is an integer, which independently of any further indices e is selected from the group of integers 1, 2, 3 and 4;
each Y represents a structure element, which in the structure $Q(YZ_e)_b$ binds the polyalicyclic structure element Q with e structure elements Z, wherein each Y is selected independently of any further structure elements Y or is omitted,
(b2) one, two or a plurality of further radically polymerizable monomers from the group consisting of acrylates and methacrylates, preferably from the group of methacrylates,
wherein the ratio of the weight of component (b1) to the weight of component (b2) is in the range 1:20 through 4:1 (preferably 1:3 through 3:1),
(c) one or a plurality of initiators and/or catalysts, and
(d) optionally one or a plurality of additives.

In other words the present invention relates to a composite material, in particular a dental composite material, consisting of or comprising:
(a) a total quantity of fillers in the range >75 through 95 wt. %, in relation to the total weight of the composite material wherein the total quantity of fillers is a mixture of fillers comprising
(a1) a total quantity in the range >10 through 30 wt. % of non-agglomerated, organically surface-modified nanoparticles with an average particle size of less than 200 nm
and
(a2) a total quantity in the range of 45 through <85 wt. % of microparticles with an average particle size in the range 0.4 μm through 10 μm
and
(a3) optionally further fillers,
wherein the weight percentages given for components (a1) and (a2) relate to the total weight of the composite material,
(b) a total quantity of polymerizable monomers in the range 3 through <25 wt. %, in relation to the total weight of the composite material, wherein the total quantity of polymerizable monomers is a mixture of monomers comprising
(b1) one, two or a plurality of monomers selected from the group consisting of compounds (monomers) with the structure $Q(Y_xZ_e)_b$, wherein the following applies:
Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $Y_xZ_e$ are substituted by alkyl groups (here preferably C1-C4-alkyl), alkoxy groups (here preferably C1-C4-alkoxy), halogen atoms (here preferably F) or trifluormethyl groups,
b is an integer selected from the group of integers 1, 2, 3 and 4,
each Z represents a structure element, which independently of any further structure elements Z is selected from the group consisting of

—O—(C=O)—CH=CH$_2$,—O—(C=O)—C(CH$_3$)=CH$_2$,

—(C=O)—CH=CH$_2$,—(C=O)—C(CH$_3$)=CH$_2$,

—CH=CH$_2$,—C(CH$_3$)=CH$_2$ and —O—CH=CH$_2$, each index e is an integer, which independently of any further indices e is selected from the group of integers 1, 2, 3 and 4,
each index x independently of any other indices x represents 0 or 1,
each Y in the structure $Q(Y_xZ_e)_b$ where x=1 represents a structure element, which binds the polyalicyclic structure element Q with e structure elements Z, wherein each Y is selected independently of any further structure elements Y,
(b2) one, two or a plurality of further radically polymerizable monomers from the group consisting of acrylates and methacrylates, preferably from the group of methacrylates,
wherein the other radically polymerizable monomer(s) is/are not compounds (monomers) of the structure $Q(Y_xZ_e)_b$ defined above and
wherein the ratio of the weight of component (b1) to the weight of component (b2) is in the range 1:20 through 4:1,
(c) one or a plurality of initiators and/or catalysts, and
(d) optionally one or a plurality of other additives.

All the statements below relating to the compounds of structure $Q(YZ_e)_b$ (wherein each Y is selected independently of any further structure elements Y or is omitted) and the preferred or particularly preferred configurations of the present invention indicated in connection with these compounds apply accordingly to the compounds of structure $Q(Y_xZ_e)_b$ (wherein each index x independently of any further indices x represents 0 and 1), and vice versa.

A compound according to the invention or to be used according to the invention of structure $Q(Y_xZ_e)_b$ comprises a polyalicyclic structure element Q, which is derived from a corresponding polyalicyclic hydrocarbon. In the context of the present text, this means that b hydrogen atoms of the hydrocarbon are replaced by substituents $Y_xZ_e$ (as described above), and optionally one, two or a plurality of the hydrogen atoms not substituted by $Y_xZ_e$ are substituted by alkyl groups, alkoxy groups, halogen atoms or trifluoromethyl groups. The polyalicyclic structure element Q is constituted by carbon ring atoms. Carbon atoms outside the rings are a component of substituents.

The "polyalicyclic" structure element Q is a bicyclic, tricyclic, tetracyclic, pentacyclic or hexacyclic hydrocarbon radical as defined above. The designations "bicyclic", "tricyclic", "tetracyclic", "pentacyclic" and "hexacyclic" here correspond to the IUPAC nomenclature.

In other words Q represents a saturated or olefinically unsaturated polyalicyclic structure element selected from the group consisting of bicyclic, tricyclic, tetracyclic, pentacyclic and hexacyclic hydrocarbon radicals, wherein none, one, two or a plurality of the hydrogen atoms of this polyalicyclic structure element Q not substituted by substituents $Y_xZ_e$ is or are substituted by alkyl groups (here preferably C1-C4-alkyl), alkoxy groups (here preferably C1-C4-alkoxy), halogen atoms (here preferably F) or trifluormethyl groups.

Preferably each Y represents a structure element, which in the structure $Q(Y_xZ_e)_b$ with x=1, binds the polyalicyclic structure element Q with e structure elements Z, wherein each Y is selected independently of any further structure elements Y.

A composite material according to the invention is preferably photocurable.

The total of the numerical values of the index b and the index e is preferably 3, 4, 5, 6, 7 or 8.

Our own research has surprisingly shown that a composite material according to the invention, in particular a dental composite material according to the invention, which comprises a relatively high proportion (more than 10 wt. %) of surface-modified, non-agglomerated nanoparticles (component (a1)

and one, two or a plurality of monomers of structure $Q(YZ_e)_b$ (as defined above and wherein each Y is selected independently of any further structure elements Y or is omitted) of component (b1), and one, two or a plurality of further radically polymerizable monomers from the group consisting of acrylates and methacrylates (b2) in a weight ratio of component (b1) to component (b2) in the range 1:20 through 4:1, in the cured state is characterized not only by a low polymerization shrinkage (preferably of less than 1.7 vol. %, particularly preferably less than 1.6 vol. %, measured according to the bonded disc method (Dental Materials 2004, 20, 88-95)), but also by low abrasion (preferably less than 30 μm, determined according to the ACTA method) and a high Vickers microhardness (preferably 140 or more).

Preference is for a composite material according to the invention comprising or consisting of:

(a) 80 through 95 wt. %, in relation to the total weight of the composite material, of a mixture of filler particles comprising
- (a1) >11, particularly preferably >12 through 30 wt. % of non-agglomerated, organically surface-modified nanoparticles with an average particle size of less than 100 nm (particularly preferably less than 60 nm) and
- (a2) 45 through <84 wt. %, preferably 45 through <83 wt. %, of microparticles with an average particle size of 0.4 μm through 10 μm and
- (a3) optionally further fillers, wherein the weight percentages given for components (a1) and (a2) relate to the total weight of the composite material, (b) 3 through 20 wt. %, in relation to the total weight of the composite material, of a mixture of monomers comprising
- (b1) one, two or a plurality of monomers of structure $Q(YZ_e)_b$ (as defined above and wherein each Y is selected independently of any other structure elements Y or is omitted) of component (b1), wherein Z preferably represents a —O—(C=O)—CH=CH$_2$, —O—(C=O)—C(CH$_3$)=CH$_2$, —(C=O)—CH=CH$_2$ or —(C=O)—C(CH$_3$)=CH$_2$,
- (b2) one, two or a plurality of further radically polymerizable monomers from the group consisting of acrylates and methacrylates, preferably from the group of methacrylates, wherein the ratio of the weight of component (b1) to the weight of component (b2) is in the range 1:3 through 3:1, (c) one or a plurality of initiators and/or catalysts, and (d) optionally one or a plurality of additives.

Particularly preferred is a composite material according to the invention with a ratio of the Vickers microhardness to the product of the microabrasion (measured using the ACTA method) and the polymerization shrinkage of more than 2, preferably of more than 2.5 [100/μm].

Dental composite materials according to the invention are preferably designed so that they can be used as a restorative composite material, in particular as a filling, underfilling, securing and/or stump build-up material, as a temporary crown and/or bridge material, as a prosthesis and/or relining material or as a flow material. Corresponding uses of a composite material according to the invention are preferred.

The composite material according to the invention comprises or consists of various components for which the following applies:

Constituent (a): Filler Particles

A composite material according to the invention contains an amount of filler particles of more than 75 wt. % (i.e. >75 wt. %), preferably 80 wt. % through 95 wt. %, in relation to the total weight of the composite material according to the invention. The amount of filler comprises a mixture of a first filler (a1) in the form of non-agglomerated, organically surface-modified nanoparticles with an average particle size of less than 200 nm and a second filler (a2) in the form of microparticles with an average particle size in the range 0.4 μm through 10 μm. Through the combination of (a1) nanoparticles and (a2) microparticles in the composite material according to the invention complete and even volumetric filling of the composite material is achieved. In this way both the shrinkage of the composite material as the polymer matrix cures and the sensitivity of the composite material to abrasion are reduced.

The average particle size $d_{50}$ of the filler particles to be used according to the invention of the filler component (a) of a composite material according to the invention is determined by means of light scattering (laser diffraction), preferably with a Beckman Coulter LS 13320 particle size analyzer.

Component (a1): Non-Agglomerated, Organically Surface-Modified Nanoparticles

In a composite material according to the invention the function of the nanoparticles is, inter alia, to fill the spaces between the microparticles, in order in this way to bring about an even filling of the composite material, and to increase the hardness and abrasion resistance. In connection with the present invention, nanoparticles mean particles with an average particle size of less than 200 nm. Preferably the average particle size is less than 100 nm and particularly preferably less than 60 nm. The smaller the nanoparticles are, the better they can fulfill their function of filling the spaces between the microparticles.

The amount of organically surface-modified nanoparticles with an average particle size of less than 200 nm is greater than 10 wt. % (e.g. >10 wt. %), preferably greater than 11 wt. % and particularly preferably greater than 12 wt. %. Our own research has shown that where the content of non-agglomerated, organically surface-modified nanoparticles with a particle size of less than 200 nm is 10 wt. % or less, the composite material is in individual cases no longer abrasion-resistant. This can probably be attributed, inter alia, to the fact that for a content of 10 wt. % or less of said nanoparticles the spaces between the microparticles with an average particle size of 0.4 µm through 10 µm are no longer adequately filled. On the other hand, it has been shown that where the content of non-agglomerated, organically surface-modified nanoparticles with an average particle size of less than 200 nm is more than 30 wt. %, the processability of the composite material is no longer sufficient; because of the high filler content its viscosity is then too high.

The materials for the nanoparticles to be used according to the invention are preferably oxides or mixed oxides and preferably selected from the group consisting of oxides and mixed oxides of the elements silicon, titanium, yttrium, strontium, barium, zirconium, hafnium, niobium, tantalum, tungsten, bismuth, molybdenum, tin, zinc, ytterbium, lanthanum, cerium, aluminum and mixtures thereof. Here, as explained, the preferred oxide nanoparticles are not agglomerated.

In a preferred configuration the nanoscale particles are present in non-agglomerated form, for example dispersed in a medium, in particle in monodisperse form.

In order to allow the nanoparticles to bond properly in the polymer matrix of a composite material according to the invention, the surfaces of the nanoparticles (preferably the preferred oxide nanoparticles) are organically modified, i.e. their surfaces have organic structure elements. One example of surface treatment of the fillers is the use of a silane. Methacryloxypropyltrimethoxysilane is particularly well-suited as a bonding agent.

Component (a2): Microparticles with an Average Particle Size in the Range 0.4 µm Through 10 µm In a composite material according to the invention the microparticles bring about an extensively even filling of the volume, wherein the remaining cavities between the microparticles are at least to some extent, filled by the nanoparticles described above (component (a2)). In connection with the present invention, microparticles mean particles with an average particle size of 400 nm through 10 µm. Preferably, the average particle size is less than 5 µm. Our own research has shown that the volumetric filling of the composite material that can already be achieved with the microparticles is more complete and even the smaller the microparticles are.

The microparticles of component (a2) can have a monomodal or polymodal, for example a bimodal, particle size distribution. Microparticles with a bimodal or multimodal particle size distribution are preferred according to the invention, since with these a more complete volumetric filling can be achieved than with the general use of microparticles with monomodal particle size distribution. In the case of a bi- or multimodal particle size distribution the particles from the fractions with the larger particle sizes bring about a coarse filling of the volume, while the particles from the fraction with the smaller particle sizes where possible fill the cavities between the particles from the fractions with the larger particle sizes. The cavities that still remain are filled by nanoparticles as described above.

Preferably, therefore, in a composite material according to the invention a component (a2) will be used which contains two or a plurality of fractions of microparticles wherein the average particle sizes of the fractions differ from one another.

Preferably component (a2) contains at least two microparticle fractions, wherein the average particle sizes of these differ from one another by at least 0.5 µm, preferably by at least 0.7 µm. In some configurations the difference in the average particle sizes of the microparticle fractions is at least 1.0 µm.

The microparticles of various fractions can comprise the same or different materials; here a plurality of fractions of microparticles can be present, the average particle sizes of which are approximately the same or are within a certain range, wherein the particle materials differ between the fractions.

A composite material according to the invention preferably comprises a component (a2), having one or a plurality of first microparticle fractions, which in each case has/have an average particle size in the range 1 µm through 10 µm, preferably 1 µm through 5 µm, and one or a plurality of second microparticle fractions, which in each case has/have an average particle size in the range >0.4 µm through <1 µm (e.g. larger than 0.4 µm, but smaller than 1 µm), preferably 0.5 µm through 0.8 µm.

The ratio of the total weight of the first microparticle fractions to the total weight of the second microparticle fractions is preferably in the range 1:1 through 10:1, preferably in the range 1.5:1 through 5:1.

The ratio of the average grain size of the or a first microparticle fraction to the average grain size of the or a second microparticle fraction of component (a2) is preferably in the range 1.5:1 through 10:1, preferably in the range 2:1 through 5:1.

In an particularly preferred composite material according to the invention the component (a2) comprises one or a plurality of first microparticle fractions, which in each case have an average particle size in the range 1 µm through 10 µm, preferably 1 µm through 5 µm, and one or a plurality of second microparticle fractions, which in each case have an average particle size in the range >0.4 µm through <1 µm, preferably 0.5 µm through 0.8 µm, wherein the ratio of the total weight of the first microparticle fractions to the total weight of the second microparticle fractions is in the range 1:1 through 10:1, preferably 1.5:1 through 5:1 and/or the ratio of the average grain size of the or a first microparticle fraction to the average grain size of the or a second microparticle fraction of component (a2) is in the range 1.5:1 through 10:1, preferably 2:1 through 5:1.

The base materials for the microparticles to be used according to the invention in surface-modified form are preferably selected from the group consisting of amorphous materials with a $SiO_2$, $ZrO_2$ and/or $TiO_2$ base, as well as mixed oxides, pyrogenic silica or precipitated silica, such as quartz glass ceramic or glass powder (in particular dental glass powder), barium or strontium glasses, fluoride ion-emitting glasses, oxides of aluminum or silicon, zeolites, appetites, zirconium silicates, hardly soluble metal salts such as barium sulfate or calcium fluoride and radiopaque fillers such as ytterbium fluoride.

For improved bonding in the polymer matrix of a composite material according to the invention the microparticles are preferably organically surface-modified. One example of surface treatment of the fillers is the use of a silane, leading to silanized microparticles. Methacryloxypropyltrimethoxysilane is particularly well-suited for surface treatment (as a bonding agent).

In a particularly preferred composite material according to the invention at least part of the microparticles of component (a2) is made up of organically surface-modified particles, preferably silanized particles and/or at least part of the microparticles of component (a2) is made up of dental glass particles; preferably at least part of the microparticles of component (a2) is organically surface-modified dental glass particles, preferably silanized dental glass particles.

Preferably in these cases component (a2) is characterized by a bi- or multi-modal particle size distribution, in particular a bi- or multi-modal particle size distribution with the preferred features described above.

Component (a3)—Further Fillers

Apart from components (a1) and (a2) the mixture of filler particles can also comprise further fillers as component (a3).

Thus, for example, filler materials with a strengthening effect such as glass fibers, polyamide or carbon fibers can be used. A composite material according to the invention can also contain fine particle splinters or bead polymers, wherein the bead polymers can be homo- or copolymers of organically curable monomers.

In a preferred configuration the present invention relates to a composite material according to the invention, preferably a composite material according to the invention as identified above and below as preferred, comprising:
(a) a total quantity of fillers in the range >75 through 95 wt. %, in relation to the total weight of the composite material, wherein the total quantity of fillers is a mixture of fillers comprising
  (a1) a total quantity in the range >10 through 30 wt. % of non-agglomerated, organically surface-modified nanoparticles with an average particle size of less than 200 nm, wherein these nanoparticles are not dental glass particles
  and
  (a2) a total quantity in the range of 45 through <85 wt. % of microparticles with an average particle size in the range 0.4 μm through 10 μm, wherein these microparticles are dental glass particles
  and
  (a3) optionally further fillers, wherein the further fillers are neither non-agglomerated, organically surface-modified particles nor dental glass particles,
wherein the weight percentages given for components (a1) and (a2) relate to the total weight of the composite material.

Constituent (b)—Mixture of Monomers

Within a composite material according to the invention the function of the mixture of monomers (b) is to form a matrix in which the abovementioned fillers (a) are integrated. This matrix is formed by respective radical polymerization of (b1) one, two or a plurality of monomers of structure $Q(YZ_e)_b$ (wherein each Y is selected independently of any further structure elements Y or is omitted), and of (b2) one, two or a plurality of further radically polymerizable monomers from the group consisting of acrylates and methacrylates, wherein the ratio of the weight of component (b1) to the weight of component (b2) is in the range 1:20 through 4:1 (preferably 1:3 through 3:1).

Here the polyalicyclic structure element Q of component (b1) ensures a sterically rigid and hydrophobic spine, and the other monomers of component (b2) ensure sufficient cross-linking, in particular with the surface-modified fillers. Our own investigations have shown that pastes with a lower amount of component (b2) or without component (b2) have increased abrasion, whereas pastes with a lower amount of component (b1) or without component (b1) demonstrate increased water absorption and less favorable mechanical characteristics (particularly a lower modulus of elasticity).

Component (b1): One, Two or a Plurality of Monomers of Structure $Q(YZ_e)_b$ with at Least One Polyalicyclic Structure Element The first component (b1) of the matrix-forming mixture of monomers is comprised one, two or a plurality of monomers of structure $Q(YZ_e)_b$ defined above (wherein each Y is selected independently of any other structure elements Y or is omitted), wherein Z preferably represents a structure element selected independently of any further structure elements Z from the group consisting of —O—(C=O)—CH=CH$_2$, —O—(C=O)—C(CH$_3$)=CH$_2$, —(C=O)—CH=CH$_2$ or —(C=O)—C(CH$_3$)=CH$_2$. Preference is for compounds of structure $Q(YZ_e)_b$ (wherein each Y is selected independently of any further structure elements Y or is omitted), wherein Z is selected from the group consisting of —O—(C=O)—CH=CH$_2$, —O—(C=O)—C(CH$_3$)=CH$_2$, that is to say those compounds of structure $Q(YZ_e)_b$, which have one, two or a plurality of acrylate and/or methacrylate groups, preferably two or a plurality of acrylate and/or methacrylate groups.

The polymers and composite materials obtainable with the monomers of component (b1) according to the invention or to be used according to the invention have a pronounced hydrophobia which inter alia manifests itself in very low water absorption of the polymers and composite materials. Additionally, the polymers obtainable by using the monomers of component (b1) according to the invention or to be used according to the invention are characterized by high mechanical stability which inter alia manifests itself in a high flexural strength of the polymers. The monomers of component (b1) according to the invention or to be used according to the invention, in particular according to the particularly preferred configurations and embodiments, lend themselves to processing into polymers which have both a low water absorption and a high flexural strength.

The monomers of component (b1) are copolymerizable with the further monomers of component (b2), wherein the cured polymers or molding materials have low shrinkage, high resistance to hydrolysis, low water absorption and high mechanical strength. The stated characteristics are in particular important in the area of dental engineering.

The preferred and particularly preferred compounds of component (b1) according to the invention or to be used according to the invention, in particular, allow a high degree of cross-linking and are also preferably radically cross-linkable. Due to their highly functionalized structure they have a high probability of cross-linking and polymerization.

Preferred compounds according to the invention or to be used according to the invention are those wherein Q represents a polyalicyclic structure element, preferably a saturated polyalicyclic structure element, selected from the group consisting of bicyclic and tricyclic hydrocarbon radicals, wherein preferably none of the hydrogen atoms of this polyalicyclic structure element Q not substituted by substituents $YZ_e$ is substituted.

Insofar as a compound according to the invention comprises two or a plurality of polyalicyclic structure elements, these may be identical or different.

Particularly preferred are monomers $Q(YZ_e)_b$ according to the invention or to be used according to the invention (wherein each Y is selected independently of any further structure elements Y or is omitted), the polyalicyclic structure element Q of which is derived from the following tricyclic hydrocarbons: tricyclo[5.2.1.0$^{2,6}$]decane (TCD), tricyclo[5.2.1.0$^{2,6}$]dec-3-ene or tricyclo[3.3.1.1$^{3,7}$]decane (adamantane), i.e. preference is for compounds according to the invention, which have a TCD structure, a tricyclo[5.2.1.0$^{2,6}$]dec-3-ene structure or an adamantane structure.

The stated particularly preferred compounds according to the invention or to be used according to the invention, in which the structure element Q represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo[2.2.1]heptane radical, are preferably those with a tricyclo[5.2.1.0$^{2,6}$]decane structure, a tricyclo[5.2.1.0$^{2,6}$]dec-3-ene structure, a tricyclo[3.3.1.1$^{3,7}$]decane structure or a bicyclo[2.2.1]heptane structure, in which in each case none of the hydrogen atoms of this polyalicyclic structure element Q not substituted by substituents $YZ_e$ (wherein each Y is selected independently of any further structure elements Y or is omitted) is substituted.

Particularly preferred compounds according to the invention or to be used according to the invention are those wherein the structure element Q represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo[2.2.1]heptane radical, and quite particularly preferred the structure element Q represents a tricyclo[5.2.1.0$^{2,6}$]decane radical or a tricyclo[5.2.1.0$^{2,6}$]dec-3-ene radical.

Preference is for the use of methacrylic acid or acrylic acid esters with a tricyclo[5.2.1.0$^{2,6}$]-decane or tricyclo [5.2.1.0$^{2,6}$]-decene structure element, selected from the group consisting of
8,9-bis(acyloxymethyl)tricyclo[5.2.1.0$^{2,6}$]decane
8,9-bis(methacryloyloxymethyl)tricyclo[5.2.1.0$^{2,6}$]decane
8,9-[bis(2-vinyloxyethyl)oxymethyl]tricyclo[5.2.1.0$^{2,6}$]dec-3-ene
8,9-[bis(2-vinyloxyethyl)oxymethyl]tricyclo[5.2.1.0$^{2,6}$]decane
8-hydroxymethyl-9-(2-vinyloxyethyl)oxymethyl]tricyclo [5.2.1.0$^{2,6}$]dec-3-ene
9-hydroxymethyl-8-(2-vinyloxyethyl)oxymethyl]tricyclo [5.2.1.0$^{2,6}$]dec-3-ene
8,9-bis(acryloyloxymethyl)tricyclo[5.2.1.0$^{2,6}$]dec-3-ene
8,9-bis(methacryloyloxymethyl)tricyclo[5.2.1.0$^{2,6}$]dec-3-ene
  diacrylic acid esters or dimethacrylic acid esters of compounds selected from the group consisting of:
3,8-dihydroxymethyl-tricyclo[5.2.1.0$^{2,6}$]decane
3,9-dihydroxymethyltricyclo-[5.2.1.0$^{2,6}$]decane
4,8-dihydroxymethyltricyclo[5.2.1.0$^{2,6}$]decane
3,8-dihydroxytricyclo[5.2.1.0$^{2,6}$]decane
3,9-dihydroxytricyclo-[5.2.1.0$^{2,6}$]decane
4.8-dihydroxytricyclo[5.2.1.0$^{2,6}$]decane
  methacrylic acid or acrylic acid esters of compounds from the group consisting of:
poly(hydroxymethyl)tricyclo[5.2.1.0$^{2,6}$]decanyl-siloxanes
oxyalkylated bishydroxymethyltricyclo[5.2.1.0$^{2,6}$]decane
oxyalkylated bishydroxytricyclo[5.2.1.0$^{2,6}$]decane
  urethane- or urea groups-containing methacrylic acid or acrylic acid esters of compounds selected from the group consisting of:
3,8-dihydroxymethyl-tricyclo[5.2.1.0$^{2,6}$]decane
4.8-dihydroxymethyl-tricyclo[5.2.1.0$^{2,6}$]decane
3.9-dihydroxymethyl-tricyclo[5.2.1.0$^{2,6}$]decane
4.9-dihydroxymethyl-tricyclo[5.2.1.0$^{2,6}$]decane Here in the stated compounds hydrogen in the tricyclo [5.2.1.0$^{2,6}$]-decane- or tricyclo[5.2.1.0$^{2,6}$]-decene radical can be substituted by alkyl groups (here preferably C1-C4-alkyl), alkoxy groups (here preferably C1-C4-alkoxy), halogen atoms (here preferably F) or trifluoromethyl groups.

A composite material according to the invention preferably comprises one, two or a plurality of compounds of structure $Q(YZ_e)_b$ (wherein each Y is selected independently of any further structure elements Y or is omitted) with a tricyclo [5.2.1.0$^{2,6}$]-decane or tricyclo[5.2.1.0$^{2,6}$]-decene structure element, wherein Z preferably is selected from the group consisting of —O—(C=O)—CH=CH$_2$ and —O—(C=O)—C(CH$_3$)=CH$_2$, and particularly preferably Z represents the group —O—(C=O)—C(CH$_3$)=CH$_2$.

Some of the radically polymerizable methacrylic acid or acrylic acid esters listed above with a TCD structure element are known from the prior art.

Our own research has shown that with the abovementioned monomers with at least one radically polymerizable double bond and a tricyclo[5.2.1.0$^{2,6}$]-decane structure element of component (b1) composite materials can be obtained with low polymerization shrinkage (preferably less than 1.7 vol. %, particularly preferably less than 1.6 vol. %, measured according to the bonded disc method), lower abrasion (preferably less than 30 μm, determined according to the ACTA method) and a high Vickers microhardness (preferably 140 or more).

Y is preferably a structure element that in the structure $Q(Y_xZ_e)_b$ bonds the polyalicyclic structure element Q with e structure elements Z and consists of or comprises a structure element that is selected from the group consisting of

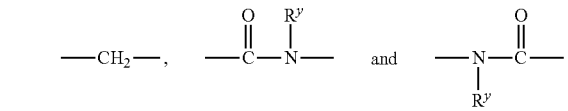

wherein R$^y$ represents another radical of the compound and wherein in each case the bond arranged to the left of the graphic formula is closer to the structure element Q and the bond arranged on the right is closer to the structure element Z.

The other radical R$^y$ of a compound of structure $Q(Y_xZ_e)_b$ according to the invention or to be used according to the invention is preferably selected from the group consisting of hydrogen, linear, branched or ring-comprising structure elements with 1 through 50 C atoms and 0 through 12 heteroatoms, wherein the heteroatoms that are optionally present are preferably selected from the group consisting of N and O.

The other radical R$^y$ here is preferably selected from the group consisting of hydrogen, linear, branched or ring-comprising structure elements with 1 through 40 C atoms and 0 through 10 heteroatoms, wherein the heteroatoms that are optionally present are preferably selected from the group consisting of N and O.

The other radical R$^y$ here is particularly preferably selected from the group consisting of hydrogen, linear, branched or ring-comprising structure elements with 1 through 35 C atoms and 1 through 10 heteroatoms, wherein the heteroatoms that are optionally present are preferably selected from the group consisting of N and O.

Here Y is preferably a structure element containing or comprising a structure element selected from the group consisting of

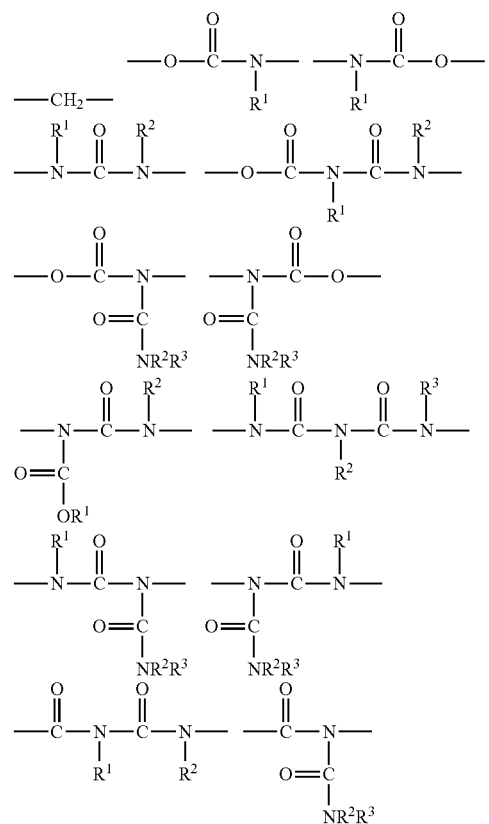

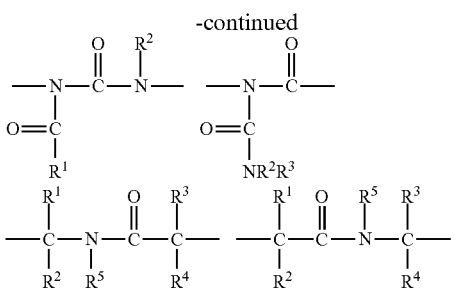

wherein $R^1$, $R^2$, $R^3$ R4 and $R^5$ represent other radicals of the compound, wherein in each case the bond arranged to the left of the graphic formula is closer to the structure element Q and the bond arranged on the right is closer to the structure element Z.

The abovementioned radicals $R^1$, $R^2$ R3, $R^4$ or $R^5$ of a compound according to the invention or a compound to be used according to the invention of structure $Q(Y_xZ_e)_b$ are, in each case independently of one another, preferably selected from the group consisting of hydrogen, linear, branched or ring-comprising structure elements with 1 through 30 C to atoms and 0 through 10 heteroatoms, wherein the heteroatoms that are optionally present are preferably selected from the group consisting of N and O.

Here the other radicals $R^1$, $R^2$, $R^3$, $R^4$ or $R^5$, in each case independently of one another, are preferably selected from the group consisting of hydrogen, linear, branched or ring-comprising structure elements with 1 through 25 C atoms and 0 through 8 heteroatoms, wherein the heteroatoms that are optionally present are preferably selected from the group consisting of N and O.

Here the other radicals $R^1$, $R^2$, $R^3$, $R^4$ or $R^5$, in each case independently of one another, are particularly preferably selected from the group consisting of hydrogen, linear, branched or ring-comprising structure elements with 1 through 20 C atoms and 0 through 5 heteroatoms, wherein the heteroatoms that are optionally present are selected from the group consisting of N and O.

In compounds of structure $Q(Y_xZ_e)_b$ according to the invention or to be used according to the invention that can be synthesized with comparatively low effort Y is a structure element, containing a structure element or consisting of this, which is selected from the group consisting of

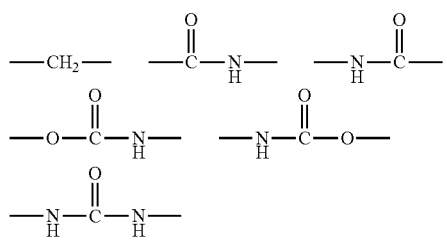

wherein in each case the bond arranged to the left of the graphic formula is closer to the structure element Q and the bond arranged on the right is closer to the structure element Z.

The compounds of structure $Q(Y_xZ_e)_b$ according to the invention or to be used according to the invention can be obtained by the preparation methods known to a person skilled in the art.

Compounds according to the invention or to be used according to the invention of structure $Q(Y_xZ_e)_b$ with an amide structure element can for example be obtained by reacting (i) an educt compound with an isocyanate group and (ii) an educt compound with a carboxylic acid group.

Compounds according to the invention or to be used according to the invention of structure $Q(Y_xZ_e)_b$ with a urethane structure element can for example be obtained by reacting (i) an educt compound with an isocyanate group and (ii) an educt compound with an alcohol group.

Compounds according to the invention or to be used according to the invention of structure $Q(Y_xZ_e)_b$ with a urea structure element can for example be obtained by reacting (i) an educt compound with an isocyanate group and (ii) an educt compound with an amino group.

Compounds according to the invention or to be used according to the invention of structure $Q(Y_xZ_e)_b$ with an allophanate structure element can for example be obtained by reacting (i) an educt compound with a urethane group and (ii) an educt compound with an isocyanate group.

Compounds according to the invention or to be used according to the invention of structure $Q(Y_xZ_e)_b$ with a biuret structure element can for example be obtained by reacting (i) an educt compound with a urea group and (ii) an educt compound with an isocyanate group.

Compounds according to the invention or to be used according to the invention of structure $Q(Y_xZ_e)_b$ with an N-acyl urea structure element can for example be obtained by reacting (i) an educt compound with an amide group and (ii) an educt compound with an isocyanate group.

In a preferred configuration of a composite material according to the invention component (b1) is selected so that this comprises or consists of bis(methacryloyloxymethyl)tricyclo[5.2.1.0$^{2,6}$]decane and/or bis(acryloyloxymethyl)tricyclo[5.2.1.0$^{2,6}$]decane.

In composite materials according to the invention the methacrylic acid esters, because of their greater biocompatibility are preferred to the corresponding acrylic acid esters, i.e. the Z in compounds of structure $Q(YZ_e)_b$ (wherein each Y is selected independently of any further structure elements Y or is omitted) preferably represents —O—(C═O)—C(CH$_3$)═CH$_2$.

Further preferred compounds (monomers) of structure $Q(YZ_e)_b$, (wherein each Y is selected independently of any further structure elements Y or is omitted) of component (b1) are those with one, two, three, four or a plurality of functional groups selected from the group consisting of urethane, urea, N-acyl urea, allophanate, biuret and amide, wherein the amide function is not directly linked with an N atom, an O atom or a carbonyl group.

EP 1 238 993 describes a method for producing polyisocyanates containing acyl urea groups and mixtures of these and their use as starting components for the preparation of polyurethane synthetic materials.

EP 0 209 700 A2 and DE 35 22 005 describe (meth)acrylic acid derivatives of certain tricyclodecenes with divalent bridge members from the group of urethanes or ureas, which can be used in the area of dentistry.

EP 0 000 194 A1 (corresponding to U.S. Pat. No. 4,160, 080) describes polyisocyanates, containing allophanate groups. These allophanate polyisocyanates may be used for the preparation of polyurethane foams, elastomers, duromers, coatings, adhesives and lacquers.

EP 0 682 012 B1 relates to a method for the preparation of bright-colored, light stable (cyclo-aliphatic) polyisocyanates comprising allophanate groups, by reacting organic compounds having urethane groups with organic polyisocyanates with (cyclo)aliphatically bonded isocyanate groups in the presence of tin(II) salts. The polyisocyanates described in EP0 682 012 B1 can be used as synthesis components in the preparation of polyurethane synthetic materials.

EP 1 727 846 B1 discloses a method for the preparation of binding agents containing allophanate groups, comprising groups reacting with ethylenically unsaturated compounds under polymerization under the effects of actinic radiation.

EP 0 712 840 B1 relates to a method for producing certain polyisocyanates containing allophanate groups through the reaction of compounds comprising urethane groups with the formation of allophanate. The compounds according to EP 0 712 840 B1 can be used as binding agents or binding agent components in coating media.

EP 0 867 457 B1 discloses an ethylenically unsaturated polyurethane, which is substantially free from isocyanate groups, which is the reaction product of an ethylenically unsaturated polyisocyanate, containing allophanate groups and β,γ-ethylenically unsaturated ether groups, with a hydroxyfunctional, ethylenically unsaturated compound, wherein the ethylenically unsaturated polyisocyanate is prepared by allophantization of the urethane groups-containing reaction products of an organic diisocyanate with β,γ-ethylenically unsaturated ether alcohol, which is selected from the group consisting of glycerin diallyl ether, trimethylolpropane diallyl ether and pentaerythritriallyl ether. The ethylenically unsaturated polyurethanes with allophanate groups disclosed in EP 0 867 457 B1 can be used as binding agents in single component coating compositions.

DE 10 2007 040 240 A1 and EP 1 645 582 A1 in each case describe a method for the preparation of radiation-curing allophanates through the reaction of compounds containing isocyanate groups and hydroxyfunctional compounds, wherein the ratio of NCO groups to OH groups is 1.45:1.0 through 1.1:1.0. According to DE 10 2007 040 239 A1 with the use of certain mixtures containing hydroxyethylacrylate and hydroxypropylacrylate as the hydroxyfunctional compounds corresponding radiation-curing allophanates are obtained. The radiation-curing allophanates according to these three documents can be used for the preparation of coatings and lacquers, as well as adhesives, inks, casting resins, dental compounds, release agents, photoresists, stereolithography systems, resins for composites and sealants.

DE 10 2004 060 285 A1 relates to radiation-curable compounds based on a dicidol mixture (containing two or three isomers 3,8-, 4,8- and/or 5,8-bis(hydroxymethyl)tricyclo [5.2.1.0$^{2,6}$]decane) with at least one compound, having at least one ethylenically unsaturated grouping with simultaneously at least one reactive grouping in relation to dicidol, wherein this compound may be a reaction product of hydroxyalkyl(meth)acrylate and diisocyanate. The compositions according to DE 10 2004 060 285 A1 can be used as radiation-induced-curing coating materials, adhesives, laminations, printing and other inks, polishes, varnishes, pigment pastes, fillers, cosmetic materials, packaging materials and/or sealing and/or insulating materials.

WO 2006/063891 A1 discloses radically polymerizable compounds, substantially containing the reaction product of a dicidol mixture and at least one compound, which has at least one ethylenically unsaturated grouping with simultaneously at least one reactive grouping in relation to dicidol. The areas of application correspond to those mentioned in DE 10 2004 060 285 A1.

U.S. Pat. No. 6,670,499 B1 describes diurethanes derived from adamantane. The compounds described in U.S. Pat. No. 6,670,499 are suitable as intermediate products for use in dentistry or for producing optical materials (such as lenses, for example).

In the area of dental engineering there is a constant need for more low-shrinkage radically polymerizable monomers. Thus a further object for the present invention was to provide novel, radically polymerizable monomers, which in a composite material according to the invention, in particular in a dental composite material according to the invention, can be used as a constituent of component (b1).

Within the context of the present text (meth)acrylic means both acrylic and methacrylic.

This further object is achieved by a compound of structure $Q(YZ_e)_b$ (wherein each Y is selected independently of any further structure elements Y) with one, two, three, four or a plurality of functional groups selected from the group consisting of N-acyl urea, allophanate, biuret and amide, wherein the amide function is not directly linked with an N atom, an O atom or a carbonyl group, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $YZ_e$ are substituted by alkyl groups (here preferably C1-C4-alkyl), alkoxy groups (here preferably C1-C4-alkoxy), halogen atoms (here preferably F) or trifluormethyl groups, b is an integer selected from the group of integers 2, 3, 4, each Z represents a structure element, which independently of any further structure elements Z is selected from the group consisting of

—O—(C=O)—CH=CH$_2$, —O—(C=O)—C(CH$_3$)=CH$_2$,

—(C=O)—CH=CH$_2$, —(C=O)—C(CH$_3$)=CH$_2$,

—CH=CH$_2$, —C(CH$_3$)=CH$_2$ and —O—CH=CH$_2$, each index e is an integer, which independently of any other indices e is selected from the group of integers 1, 2, 3 and 4, each Y represents a structure element, which in the structure $Q(YZ_e)_b$ bonds the polyalicyclic structure element Q with e structure elements Z, wherein the compound is a first reaction product of a first reaction of A) a compound of structure $QG_b$, in which each G represents a reactive group, which independently of other groups G is selected from the group consisting of (—CH$_2$)$_n$—NH$_2$, (—CH$_2$)$_n$—(OCH$_2$—CHR)$_m$—OH, (—CH$_2$)$_n$—NCO and (—CH$_2$)$_n$—COOH with B) two or a plurality of identical or different compounds MZ$_e$, wherein M represents a structure element which in each case has one or a plurality of grouping(s) that react with the groups G selected from the group consisting of —NH, —NH$_2$, —OH, —NCO and —COOH, wherein the following applies:

R, in each case independently of any further R, represents a hydrogen atom or an alkyl radical; preferably R represents a hydrogen atom or a linear or branched alkyl radical with 1 through 6 C atoms; more preferably R represents a hydrogen atom or a methyl radical, m is an integer selected from the group of integers from 0 through 10, each index n is an integer, which independently of any further indices n is selected from the group consisting of 0 and 1, or the compound is a second reaction product from a reaction of the above first reaction product with C) a further compound according to A) or B), wherein each further compound according to A) or B) has the above meaning, independently of what A) and/or B) represent in the first reaction, or the compound is a third reaction product from a reaction of the above second reaction product with D) a further compound according to A) or B), wherein each further compound according to A) or B) has the above meaning, independently of what A) and/or B) represent in the first and/or second reaction.

From that stated above it can be inferred that for compounds according to the invention, containing an amide group (as defined) this amide group is not a component of the urethane group.

Also preferred are compounds according to the invention of structure $Q(YZ_e)_b$ (wherein each Y is selected independently of any other structure elements Y) of component (b1) with one, two, three, four or a plurality of functional groups selected from the group consisting of N-acyl urea, allophanate, biuret and amide, wherein the amide function is not directly linked with an N atom, an O atom or a carbonyl group, wherein the amide in turn preferably represents (meth)acrylamide.

In preferred compounds according to the invention of structure $Q(YZ_e)_b$ (wherein each Y is selected independently of any further structure elements Y), the linking between Q and at least one structure element takes place via a bridge which contains or comprises a divalent bridge member, selected from the group consisting of

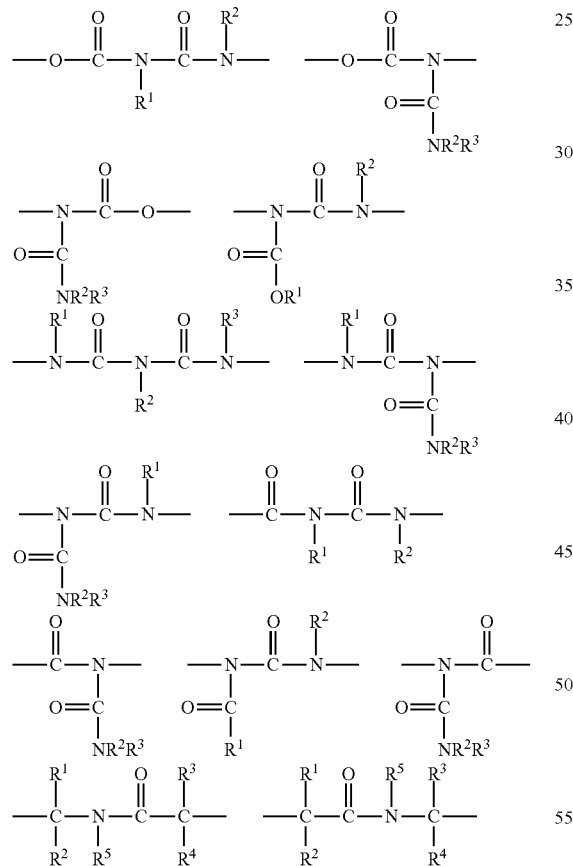

wherein $R^1$, $R^2$, $R^3 R^4$, $R^5$ represent other radicals of the compound, wherein in each case the bond arranged to the left of the graphic formula is closer to the structure element Q and the bond arranged on the right is closer to the structure element Z.

The further object is likewise achieved by novel compounds of structure $Q(Y_xZ_e)_b$ with x=1 with one, two, three, four or a plurality of functional groups that are selected from the group consisting of N-acyl urea, allophanate and biuret, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein none, one, two or a plurality of the hydrogen atoms of this polyalicyclic structure element Q not substituted by substituents $YZ_e$ is or are substituted by alkyl groups, alkoxy groups, halogen atoms or trifluormethyl groups;

b is an integer selected from the group of integers 2, 3, 4;

each Z represents a structure element, which independently of any further structure elements Z is selected from the group consisting of

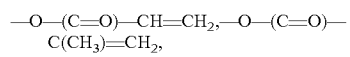

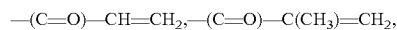

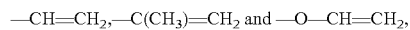

each index e is an integer, which independently of any further indices e is selected from the group of integers 1, 2, 3 and 4;

each Y represents a structure element that in the structure $Q(Y_xZ_e)_b$ with x–1 bonds the polyalicyclic structure element Q with e structure elements Z and contains or consists of a structure element selected from the group consisting of

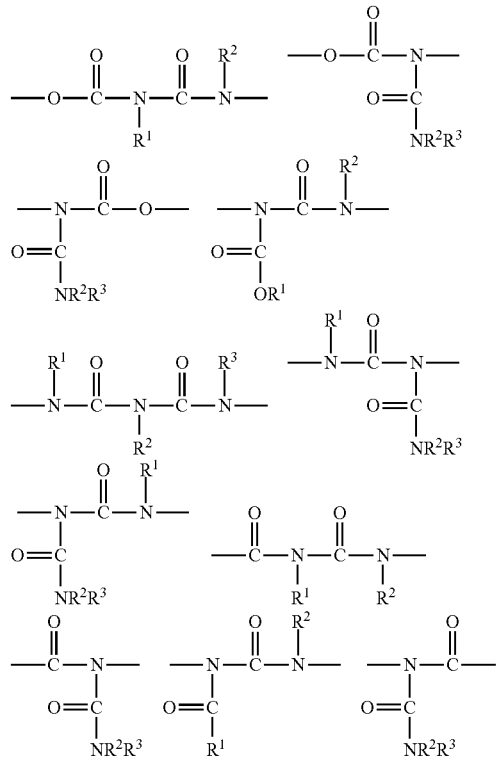

wherein $R^1$, $R^2$, and $R^3$ represent other radicals of the compound, wherein in each case the bond arranged to the left of the graphic formula is closer to the structure element Q and the bond arranged on the right is closer to the structure element Z. These compounds according to the invention are in particular suitable as monomers for use in composite materials according to the invention.

Preferably such a compound according to the invention of structure $Q(Y_xZ_e)_b$ with x=1 comprises two, three, four or a plurality of functional groups selected from the group consisting of N-acyl urea, allophanate and biuret.

In a preferred configuration each index e represents an integer, which independently of any further indices e is selected from the group of integers 2, 3 and 4.

The abovementioned radicals $R^1$, $R^2$ or $R^3$ of a novel compound according to the invention are, in each case independently of one another, preferably selected from the group consisting of hydrogen, linear, branched or ring-comprising structure elements with 1 through 30 C atoms and 0 through 10 heteroatoms, wherein the heteroatoms that are optionally present are preferably selected from the group consisting of N and O.

The other radicals $R^1$, $R^2$ or $R^3$ of a novel compound according to the invention are, in each case independently of one another, preferably selected from the group consisting of hydrogen, linear, branched or ring-comprising structure elements with 1 through 25 C atoms and 0 through 8 heteroatoms, wherein the heteroatoms that are optionally present are preferably selected from the group consisting of N and O.

The other radicals $R^2$ or $R^3$ of a novel compound according to the invention are, in each case independently of one another, preferably selected from the group consisting of hydrogen, linear, branched or ring-comprising structure elements with 1 through 20 C atoms and 0 through 5 heteroatoms, wherein the heteroatoms that are optionally present are selected from the group consisting of N and O.

A novel compound according to the invention $Q(Y_xZ_e)_b$ with x=1, preferably a compound according to the invention $Q(Y_xZ_e)_b$ with x=1 as identified above as preferred, can preferably be prepared by reacting a first reaction product, which is the reaction product of a first reaction of A) a compound of structure $QG_b$, in which each G represents a reactive group, which independently of further groups G is selected from the group consisting of $(-CH_2)_n-NH_2$, $(-CH_2)_n-(OCH_2-CHR)_m-OH$, $(-CH_2)_n-NCO$ and $(-CH_2)_n-COOH$ with B) two or a plurality of identical or different compounds $MZ_e$, wherein M represents a structure element which in each case has one or a plurality of grouping(s) that react with the groups G selected from the group consisting of —NH, —NH$_2$, —OH, —NCO and —COOH, wherein the following applies:
R in each case independently of any other R represents a hydrogen atom or an alkyl radical;
m is an integer selected from the group of integers from 0 through 10,
each index n is an integer, which independently of any further indices n is selected from the group consisting of 0 and 1, wherein the compound is a second reaction product from a reaction of the above first reaction product with C) a further compound according to A) or B), wherein each further compound according to A) or B) has the above meaning, independently of what A) and/or B) represent in the first reaction, or the compound is a third reaction product from a reaction of the above second reaction product with D) a further compound according to A) or B), wherein each further compound according to A) or B) has the above meaning, independently of what A) and/or B) represent in the first and/or second reaction.

A compound according to the invention in a preferred configuration is a second reaction product from a reaction of the above first reaction product with C) a further compound according to A) or B), wherein each further compound according to A) or B) has the same meaning as in the first reaction, and/or wherein the compound is a third reaction product from a reaction of the above second reaction product with D) a further compound according to A) or B), wherein each further compound according to A) or B) has the same meaning as in the first and/or the second reaction, preferably as in the first and the second reaction.

In a first preferred embodiment m=0. This applies to all aspects of the present invention.

In preferred compounds according to the invention the link between Q and at least one structure element Z takes place via a bridge which contains or consists of a divalent bridge member, selected from the group consisting of

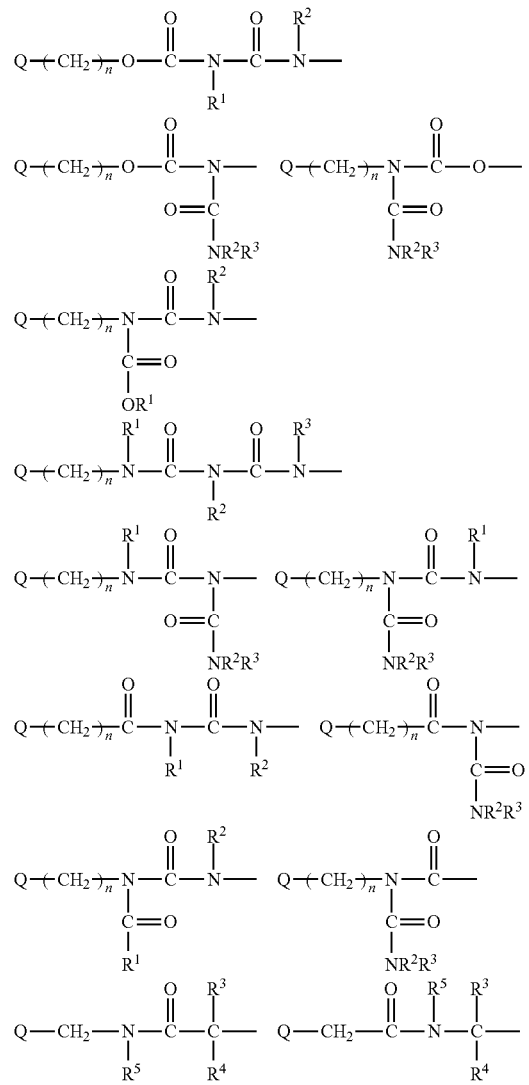

wherein $R^1$, $R^2$, $R^3$, $R^4$, $R^5$ represent other radicals of the compound and Q and the index n have the meaning indicated above.

The bond shown on the right of each graphic formula is closest to the structure element Z.

In a preferred configuration a novel compound according to the invention $Q(Y_xZ_e)_b$ with x=1, preferably a compound according to the invention $Q(Y_xZ_e)_b$ with x=1 as identified above or below as preferred, comprises one or a plurality of structure elements selected from the group consisting of

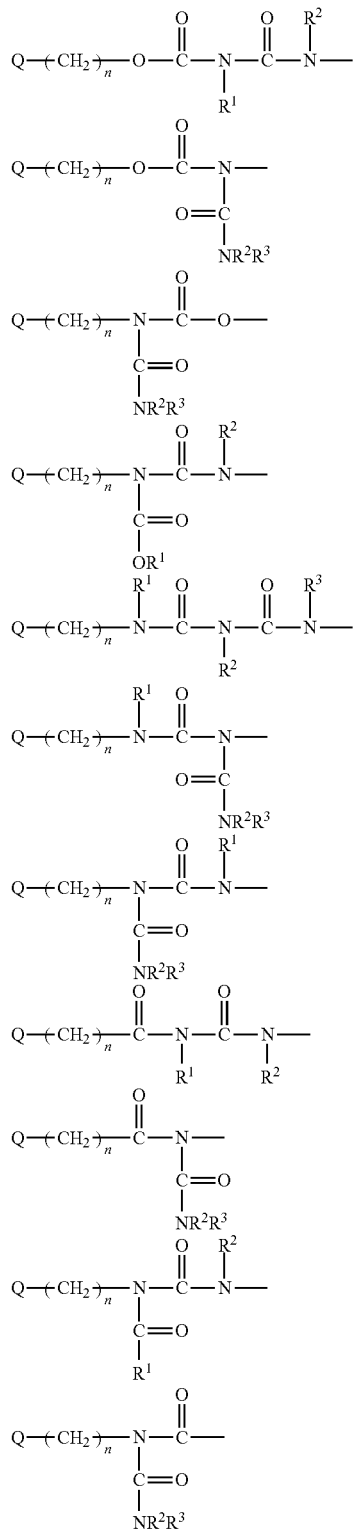

wherein $R^1$, $R^2$ and $R^3$ represent other radicals of the compound (and preferably have the abovementioned preferred meaning) and Q has the abovementioned meaning and the index n is selected from the group consisting of 0 and 1.

As already mentioned above preferred novel compounds according to the invention are those wherein Q represents a saturated polyalicyclic structure element, selected from the group consisting of bicyclic and tricyclic hydrocarbon radicals, wherein preferably none of the hydrogen atoms of this polyalicyclic structure element Q not substituted by $YZ_e$ substituents is substituted.

Particularly preferred novel compounds according to the invention are those wherein the structure element Q represents a tricyclo$[5.2.1.0^{2,6}]$decane radical, a tricyclo$[5.2.1.0^{2,6}]$dec-3-ene radical, a tricyclo$[3.3.1.1^{3,7}]$decane radical or a bicyclo$[2.2.1]$heptane radical.

Preferred novel compounds according to the invention or to be used according to the invention of component (b1) are those wherein Q represents a tricyclic hydrocarbon radical, wherein preferably none of the hydrogen atoms of this tricyclic hydrocarbon radical not substituted by substituents $YZ_e$ (wherein each Y is selected independently of any further structure elements or is omitted) is substituted.

Particularly preferred novel compounds according to the invention are those wherein the structure element Q represents a tricyclo$[5.2.1.0^{2,6}]$decane radical, a tricyclo$[5.2.1.0^{2,6}]$dec-3-ene radical or a tricyclo$[3.3.1.1^{3,7}]$decane radical, more preferably a tricyclo$[5.2.1.0^{2,6}]$decane radical or a tricyclo$[3.3.1.1^{3,7}]$decane radical.

Preference is for novel compounds according to the invention in which
(i) the structure element Z represents —O—(C═O)—C($CH_3$)═$CH_2$, wherein the functional groups are allophanate, biuret or acyl urea groups, since with these compounds particularly good results have been obtained,
and/or
(ii) the structure element Q represents a tricyclo$[5.2.1.0^{2,6}]$decane radical.

Greater preference is for novel compounds according to the invention, in which the structure element Z represents —O—(C═O)—C($CH_3$)═$CH_2$, wherein the functional groups are allophanate, biuret or acyl urea groups and the structure element Q represents a tricyclo$[5.2.1.0^{2,6}]$decane radical.

Preference is for novel compounds according to the invention in which all photocurable groups present correspond to the structure element Z.

Preference is for novel compounds according to the invention in which all terminal polymerizable groups present correspond to the structure element Z.

A novel compound according to the invention, apart from photocurable groups of the structure element Z, can also comprise other polymerizable, preferably terminal polymerizable groups, which are not photocurable, in particular not under the normal photocuring conditions that exist in dentistry. This is generally not preferred, however, since such groups do not contribute towards the desired characteristics of the product that exists following polymerization.

Further preferred compounds according to the invention are those in which at least one structure element $YZ_e$ is selected independently of the further structure elements $YZ_e$, and preferably all structure elements $YZ_e$ are selected from the group consisting of

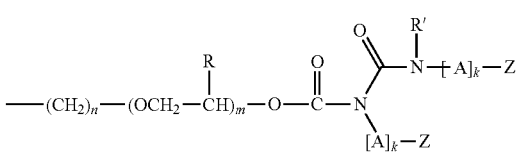

-continued

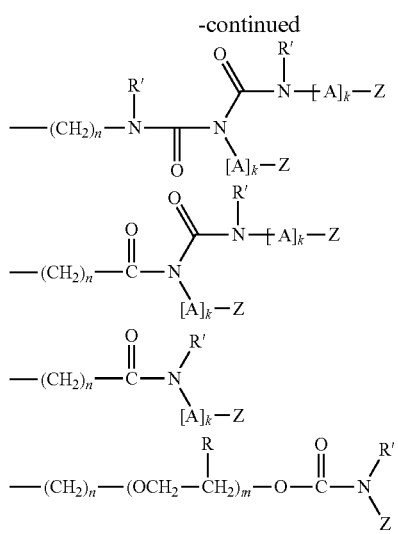

wherein Z, R, m and n have the meaning given above and wherein the following also applies:

each A represents a divalent organic bridge member, each index k is an integer, which independently of any further indices k is selected from the group consisting of 0 and 1;

each R' represents a structure element which independently of any further structure elements R' is selected from the group consisting of H and a structure element (C=O)—NH-(A)$_k$-Z, wherein A, Z and k in turn have the meanings given above.

In a preferred embodiment m=0.

Similarly preferred compounds according to the invention are those in which at least one structure element YZ$_e$ is selected independently of the further structure elements YZ$_e$, and preferably all structure elements YZ$_e$ are selected from the group consisting of

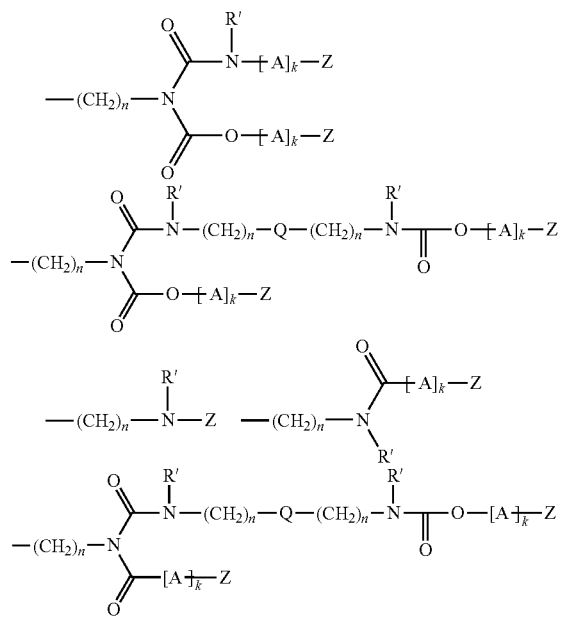

-continued

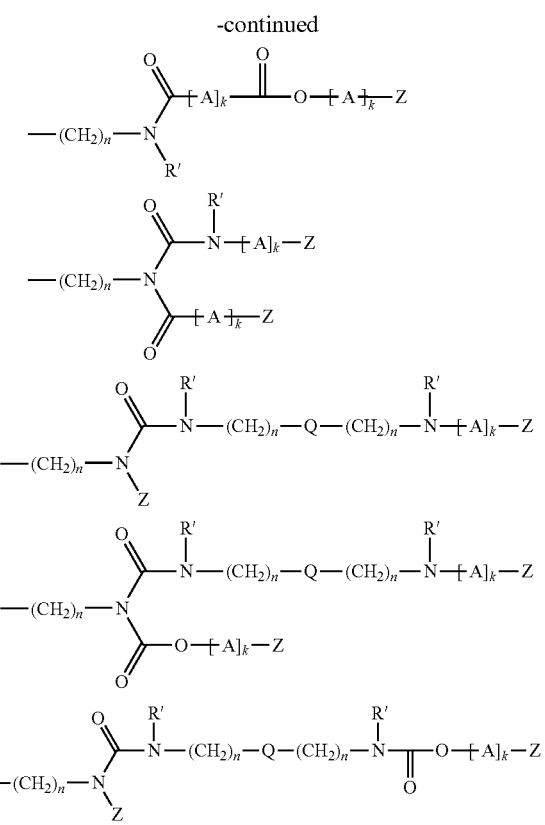

wherein each Q independently of any further structure elements Q has the above meaning and wherein Z, A, k and R', as well as n, have the above meaning.

In a preferred configuration the present invention relates to a compound according to the invention Q(Y$_x$Z$_e$)$_b$ with x=1, preferably a compound according to the invention Q(Y$_x$Z$_e$)$_b$ with x=1 as identified above or below as preferred, wherein at least one structure element YZ$_e$ is selected independently of the further structure elements) YZ$_e$, and preferably all structure elements YZ$_e$ are selected from the group consisting of

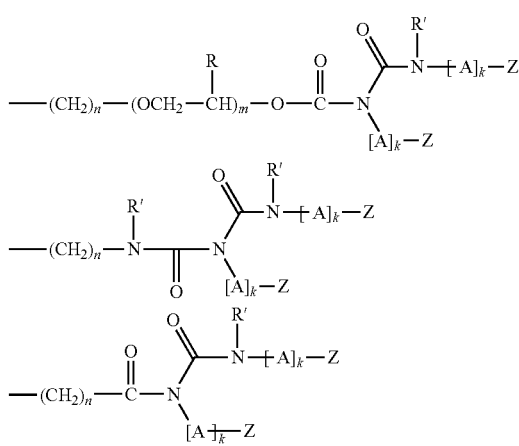

-continued

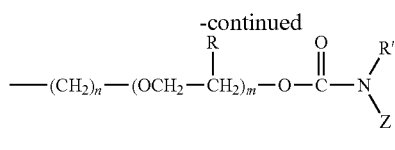

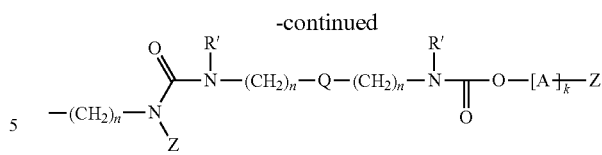

wherein Z, R, m and n have the meaning given above and wherein the following also applies:

each A represents an organic structure element, each index k is an integer, which independently of any further indices k is selected from the group consisting of 0 and 1;

each R' represents a structure element which independently of any further structure elements R' is selected from the group consisting of H and a structure element (C=O)—NH-(A)$_x$-Z, wherein A, Z and k in turn have the meanings given above.

In a preferred configuration the present invention relates to a novel compound according to the invention $Q(Y_xZ_e)_b$ with x=1, preferably a compound according to the invention $Q(Y_x\text{-}Z_e)_b$ with x=1 as identified above or below as preferred, wherein at least one structure element $YZ_e$ is selected independently of the further structure element(s) $YZ_e$, and preferably all structure elements $YZ_e$ are selected from the group consisting of

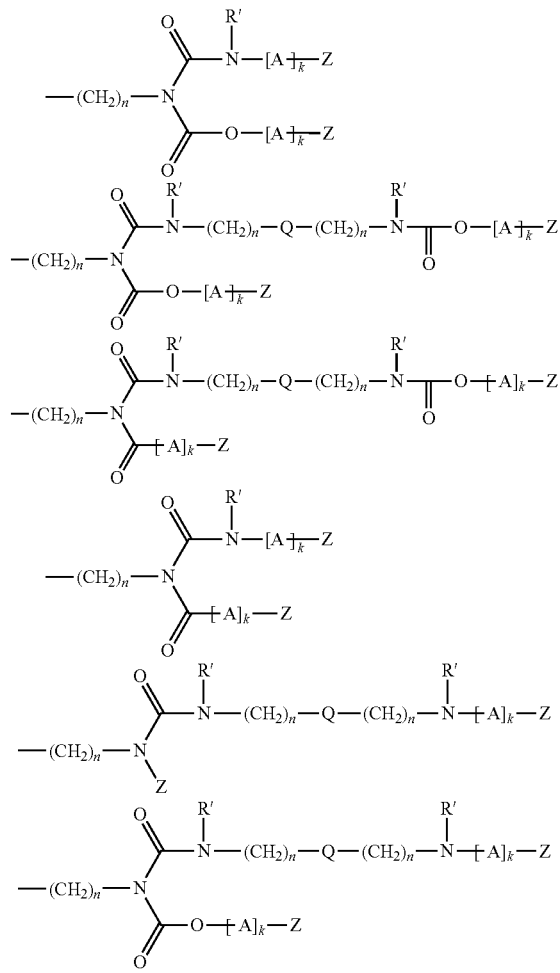

wherein each Q independently of any further structure elements Q has the above meaning, and wherein Z and n have the abovementioned meaning and wherein the following also applies:

each A represents an organic structure element, each index k is an integer, which independently of any further indices k is selected from the group consisting of 0 and 1;

each R' represents a structure element which independently of any further structure elements R' is selected from the group consisting of H and a structure element (C=O)—NH-(A)$_k$-Z, wherein A, Z and k in turn have the meanings given above.

Here in turn preference is for compounds to be used according to the invention in which each structure element A independently of any further structure elements A is selected from the group consisting of all linear, branched or ring-comprising divalent organic bridge members with 1 through 25 C atoms and optionally 1 through 10, preferably 1 through 5 heteroatoms, wherein the heteroatoms that are optionally present are preferably selected from the group consisting of N and O.

Here in turn preference is for a compound according to the invention in which each structure element A independently of any further structure elements A is selected from the group consisting of linear, branched or ring-comprising structure elements with 1 through 25 C atoms and 0 through 10 heteroatoms, preferably with 1 through 5 heteroatoms, wherein the heteroatoms that are optionally present are preferably selected from the group consisting of N and O.

Further preference is for compounds in which each structure element A independently of any other structure elements A is selected from the group consisting of ($C_1$-$C_{20}$) alkylene, ($C_1$-$C_{20}$) heteroalkylene, ($C_3$-$C_{20}$) cycloalkylene, ($C_4$-$C_{20}$) cycloalkylalkyene, ($C_2$-$C_{20}$) alkenylene, ($C_3$-$C_{20}$) cycloalkenylene, $CC_4$-$C_{20}$) cycloalkenylalkylene, ($C_4$-$C_{20}$) cycloalkenylenalkylene, ($C_3$-$C_{25}$) arylene, ($C_2$-$C_{25}$) heteroarylene, ($C_4$-$C_{25}$) arylalkylene, $C_4$-$C_{25}$) arylenealkylene, ($C_4$-$C_{25}$) arylheteroalkylene, and ($C_4$-$C_{25}$) arylenheteroalkylene.

In preferred configurations structure element A comprises one or a plurality of the following atoms or groups of atoms:

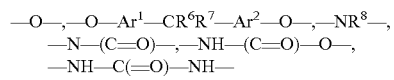

wherein the following applies:

$Ar^1$ and $Ar^2$ independently of each other represent an aromatic ring which is optionally substituted, here preferably once or a plurality of times substituted with C1-C4 alkyl radicals, here in turn preferably a phenyl ring, $R^6$, $R^7$ and $R^8$ independently of one another represent hydrogen or a C1-C8 radical, here preferably a C1-C4 alkyl radical, here in turn preferably methyl or ethyl.

The present invention further relates to a method for preparing a compound according to the invention $Q(YZ_e)_b$ (wherein each Y is selected independently of any further structure elements Y) or a mixture, comprising at least one such compound according to the invention $Q(YZ_e)_b$, with the following steps:

In a first reaction, reaction of

A) a compound of structure $QG_b$, in which each G represents a reactive group, which is selected independently of further G groups from the group consisting of $(-CH_2)_n-NH_2$, $(-CH_2)_n-(OCH_2-CHR)_m-OH$, $(-CH_2)_n-NCO$ and $(-CH_2)_n-COOH$, preferably a compound of structure $QG_b$, in which each G represents a reactive group, which is selected independently of further G groups from the group consisting of $-NH_2$, $-CH_2NH_2$, $-OH$, $-CH_2OH$, $-NCO$, $-CH_2NCO$, and $-COOH$, with B) two or a plurality of identical or different compounds $MZ_e$, wherein M represents a structure element which in each case has one or a plurality of grouping(s) that react with the groups G selected from the group consisting of $-NH$, $-NH_2$, $-OH$, $-NCO$ and $-COOH$ to form a first reaction product, optionally in a second reaction, reaction of the first reaction product with C) a further compound according to A) or B), wherein each further compound according to A) or B) has the above meaning, independently of what A) and/or B) represent in the first reaction, to form a second reaction product, and optionally in a third reaction, reaction of the second reaction product with D) a further compound according to A) or B), wherein each further compound according to A) or B) has the above meaning, independently of what A) and/or B) represent in the first and/or second reaction.

wherein Q, b, Y, Z, and e in each case have the above meanings, and wherein the following applies:

R, in each case independently of any other R, represents a hydrogen atom or an alkyl radical; preferably R represents a hydrogen atom or a linear or branched alkyl radical with 1-6 C atoms; more preferably R represents a hydrogen atom or a methyl radical;

m is an integer selected from the group of integers from 0 through 10, each index n is an integer, which independently of any other indices n is selected from the group consisting of 0 and 1, wherein the ratio of the total number of NCO groups to the total number of $-NH_2$, $-OH$ and $-COOH$ in the total number of compounds according to A) and B) in the first, optionally second and optionally third reaction is greater than or equal to 1, preferably in the range 1.1:1 through 5:1, more preferably in the range 1.25:1 through 4:1, particularly preferably in the range 1.5:1 through 3:1, and most preferably in the range 2:1 through 2.5:1.

A preferred method according to the invention for preparing a compound according to the invention $Q(Y_xZ_e)_b$ with x=1, preferably a compound according to the invention $Q(Y_xZ_e)_b$ with x=1 identified above or below as preferred, or a mixture comprising at least one such compound $Q(Y_xZ_e)_b$ is a method with the following steps:

In a first reaction, reaction of

A) a compound of structure $QG_b$, in which each G represents a reactive group, which independently of further groups G is selected from the group consisting of $(-CH_2)_n-NH_2$, $(-CH_2)_n(OCH_2-CHR)_n-OH$, $(-CH_2)_n-NCO$ and $(-CH_2)_n-COOH$ with B) two or a plurality of identical or different compounds $MZ_e$, wherein M represents a structure element which in each case has one or a plurality of grouping(s) that react with the groups G selected from the group consisting of $-NH$, $-NH_2$, $-OH$, $-NCO$ and $-COOH$ to form a first reaction product, in a second reaction, reaction of the first reaction product with C) a further compound according to A) or B), wherein each further compound according to A) or B) has the above meaning, independently of what A) and/or B) represent in the first reaction, to form a second reaction product, and optionally in a third reaction, reaction of the second reaction product with D) a further compound according to A) or B), wherein each further compound according to A) or B) has the above meaning, independently of what A) and/or B) represent in the second reaction, wherein Q, b, Y, Z, e, M, R, m and n in each case have the above meanings, and wherein the ratio of the total number of NCO groups to the total number of $-NH_2$, $-OH$ and $-COOH$ in the total number of compounds according to A) and B) in the first, the second and optionally third reaction is greater than or equal to 1, preferably in the range 1.1:1 through 5:1, more preferably in the range 1.25:1 through 4:1, particularly preferably in the range 1.5:1 through 3:1, and most preferably in the range 2:1 through 2.5:1.

In a method according to the invention for preparation of a compound according to the invention $Q(Y_xZ_e)_b$ with x=1, preferably a compound according to the invention $Q(Y_xZ_e)_b$ with x=1 identified above or below as preferred, or a mixture comprising at least one such compound $Q(Y_xZ_e)_b$, the ratio of the total number of NCO groups reacted to the total number of $-NH_2$, $-OH$ and $-COOH$ reacted in the total number of compounds according to A) and B) in the first, second and optionally third reaction is preferably in the range 1.1:1 through 5:1, more preferably in the range 1.25:1 through 4:1, particularly preferably in the range 1.5:1 through 3:1, and most preferably in the range 2:1 through 2.5:1.

Preferably the reaction to the first reaction product, to the second reaction product and/or to the third reaction product takes place in the presence of a catalyst.

Preferred catalysts here are tertiary amines or Lewis acids, here in turn preference is for metal salts of higher fatty acids, in particular dibutyltin dilaurate or tin (II) octoate The quantity of catalyst here is preferably in the range 0.01 through 2 wt. %, preferably 0.08 through 1 wt. %, in relation to the total quantity of reactants according to A) and B) and optionally C) and optionally D).

The reaction to the first reaction product, to the second reaction product and/or the third reaction product preferably takes place in a temperature range of 0 through 160° C., preferably in the range 30 through 140° C. and particularly preferably in the range 60 through 120° C. The reaction is preferably carried out at normal pressure (1013 mbar).

In a further aspect the present invention relates to a mixture comprising one, two or a plurality of different compounds according to the invention that are preparable using a method according to the invention.

The present invention further relates to the use of a compound according to the invention, preferably in one of the configurations characterized as preferred or particularly preferred, in a composite material, preferably in a dental composite material.

The present invention also relates to the use of a compound according to the invention, preferably in one of the configurations identified as preferred or particularly preferred, for the preparation of a composite material, preferably a dental composite material, in particular a restorative composite material, here preferably as a filling, underfilling, securing and/or stump build-up material, as a temporary crown and/or bridge material, as a prosthesis and/or lining material or as a flow material.

In addition the present invention relates to a compound according to the invention, preferably in one of the configurations identified as preferred or particularly preferred, as or for use as a dental material, in particular a filling, underfilling, securing and/or stump build-up material, as a temporary crown and/or bridge material, as a prosthesis and/or lining material or as a flow material.

For the preparation of the compounds according to the invention preferably hydroxyl compounds of (meth)acrylates can be used, wherein mixtures of acrylates and methacrylates can also be used. Preference (for use as reaction partners according to components B), C) and/or D)) is for:
alkylene oxide mono(meth)acrylates such as for example ethylene glycol mono(meth)acrylate, diethylene glycol mono(meth)acrylate, triethylene glycol mono(meth)acrylate, tetraethylene glycol mono(meth)acrylate, etc., polyalkylene oxide mono(meth)acrylates such as for example polyethylene glycol mono(meth)acrylate, polypropylene glycol mono(meth)acrylate, polybutylene glycol mono(meth)acrylate, etc., hydroxyalkyl mono(meth)acrylates such as for example hydroxyethyl(meth)acrylate, hydroxypropyl(meth)acrylate, 2-hydroxypropyl(meth)acrylate, hydroxybutyl(meth)acrylate, 4-hydroxybutyl(meth)acrylate, hydroxypentyl(meth)acrylate, 3-hydroxy-2,2-dimethylpropyl(meth)acrylate, hydroxyhexyl(meth)acrylate, hydroxyheptyl(meth)acrylate, hydroxyoctyl(meth)acrylate, hydroxynonyl(meth)acrylate, hydroxydecyl(meth)acrylate, hydroxyundecyl(meth)acrylate, hydroxydodecyl(meth)acrylate, etc., poly(e-caprolactone)mono(meth)acrylate, poly(γ-caprolactone)mono(meth)acrylate, etc., the mono-, di-, tetra-, or penta(meth)acrylates of polyhydric alcohols, such as glycerin, such as for example glycerin di(meth)acrylate (2-hydroxypropyl-1,3-di(meth)acrylate, 3-hydroxypropyl-1,2-di(meth)acrylate), such as trimethylolpropane, such as for example trimethylolpropane di(meth)acrylate, such as pentaerythritol, such as for example pentaerythritoltri(meth)acrylate, such as dipentaerythritol, such as for example dipentaerythritolpenta(meth)acrylate, such as ditrimethylolpropantri(meth)acrylate, such as neopentyl glycol(meth)acrylate, the (meth)acrylates of alkoxylated or phenoxylated glycerin, here preferably the (meth)acrylates of ethoxylated, propoxylated, etc. glycerin, trimethylolpropane, pentaerythritol, dipentaerythritol, ditrimethylolpropane, etc. and the technical mixtures thereof, bisphenol-A-glycidyl-(meth)acrylate (Bis-GMA), bisphenol-B-glycidyl-(meth)acrylate, bisphenol-C-glycidyl-(meth)acrylate, bisphenol-F-glycidyl-(meth)acrylate, alkoxylated bisphenol-A-glycidyl-(meth)acrylate (e.g. ethoxylated bisphenol-A-glycidyl-(meth)acrylate), etc.

For the preparation of the compounds according to the invention as component B) isocyanates can also be used. Preference here is for mono- and diisocyanates.

Preferred diisocyanates are selected from the group consisting of cyclohexane diisocyanate, methylcyclohexane diisocyanate, ethylcyclohexane diisocyanate, propylcyclohexane diisocyanate, methyldiethylcyclohexane diisocyanate, phenylene diisocyanate, toluylene diisocyanate, bis(isocyanatophenyl)methane, propane diisocyanate, butane diisocyanate, pentane diisocyanate, hexane diisocyanate, such as hexamethylene diisocyanate or 1,5-diisocyanato-2-methyl pentane, heptane diisocyanate, octane diisocyanate, nonane diisocyanate, such as 1,6-diisocyanato-2,4,4-trimethylhexane or 1,6-diisocyanato-2,2,4-trimethylhexane, nonane triisocyanate, such as 4-isocyanatomethyl-1,8-octane diisocyanate, decane di- and triisocyanate, undecane di- and -triisocyanate, dodecandi- and -triisocyanates, isophorone diisocyanate, dicyclohexylmethane-4,4'-diisocyanate, isocyanatomethylmethylcyclohexyl isocyanate, 1,3-bis(isocyanatomethyl)cyclohexane or 1,4-bis(isocyanatomethyl)cyclohexane.

Preferred monoisocyanates are (meth)acryloyl isocyanate and (meth)acryl-C2-C8-alkyl isocyanates (e.g. (meth)arylalkyl isocyanates with alkyl spacers, having 2 through 8, particularly preferably 2 through 6 carbon atoms), here in turn preference is for (meth)acryl ethyl isocyanate (2-isocyanatoethyl(meth)acrylate).

Furthermore, as component B) monoisocyanates have proven to be an advantage that are the reaction products of amino- or hydroxyalkyl(meth)acrylates, the alkyl spacers of which have 1 through 12, preferably 2 through 8, particularly preferred 2 through 6 carbon atoms, and diisocyanates.

Preferably to this end a diisocyanate mentioned above is reacted in equimolar proportions with an amino- or hydroxylalkyl compound (indicated above as preferred) of a (meth)acrylate, wherein the hydroxylalkyl compounds in turn are preferably selected from the group consisting of hydroxyethyl(meth)acrylate, hydroxypropyl(meth)acrylate, hydroxybutyl(meth)acrylate, hydroxypentyl(meth)acrylate and hydroxyhexyl(meth)acrylate.

Quoted examples are the reaction products in the molar ratio of 1:1 of hydroxyethylmethacrylate and isophorone diisocyanate, dicyclohexylmethane-4,4'-diisocyanate or hexamethylene diisocyanate.

In the following the invention is initially explained in detail for monomers comprising tricyclic structure elements Q using the example of tricyclo[5.2.1.0$^{2,6}$]decane (TCD)—derivatives.

1.) Starting with the bis(hydroxymethyl)tricyclo[5.2.1.0$^{2,6}$]decane (TCD-diol)

bis(hydroxynnethyl)tricyclo[5.2.1.0$^{2,6}$]decane is commercially available, for example as a dicidol mixture of the isomeric compounds 3,8-bis(hydroxymethyl)tricyclo[5.2.1.0$^{2,6}$]decane and 4,8-bis(hydroxymethyl)tricyclo[5.2.1.0$^{2,6}$]decane as well as 3,9-bis(hydroxymethyl)tricyclo[5.2.1.0$^{2,6}$]decane and 4,9-bis(hydroxymethyl)tricyclo[5.2.1.0$^{2,6}$]decane.

The bis(hydroxymethyl)tricyclo[5.2.1.0$^{2,6}$]decanes can, starting with dicyclopentadiene (tricyclo[5.2.1.0$^{2,6}$]deca-3,8-diene), be synthesized. Dicyclopentadiene is easily accessible in a Diels-Alder reaction by dimerization of cyclopentadiene. Hydroformylation of dicyclopentadiene then produces the bis(hydroxymethyl)tricyclo[5.2.1.0$^{2,6}$]decane. According to the synthesis route taken bis(hydroxynnethyl)tricyclo[5.2.1.0$^{2,6}$]decanes specifically substituted at different positions can be obtained. Thus in published documents JP 7-206740, EP 1 112 995 B1 or EP 0 049 631 B1 specifications are provided on how, for example, the 8,9-bis(hydroxymethyl)tricyclo[5.2.1.0$^{2,6}$]decane is preparable. DE 103 52 260 B3 on the other hand describes a method for preparing 3(4), 8(9)-bis(hydroxymethyl)tricyclo[5.2.1.0$^{2,6}$] decane. The notation of the positions of the hydroxymethyl groups 3(4), 8(9) means 3 or 4, 8 or 9.

The commercially available starting compound that can be used for the preparation of monomers according to the invention, bis(hydroxymethyl)tricyclo[5.2.1.0$^{2,6}$]decane, thus contains hydroxymethyl groups both at positions 3 or 4 and in positions 8 or 9. It is now possible by addition of alkylene oxides, in general in quantities of 1 through 10 mol, particularly of ethylene oxide, propylene oxide, butylene oxide, etc. in the presence of basic catalysts and according to known methods to synthesize the corresponding polyether polyols. EP 0 023 686 B1 contains more detailed preparation specifications in this connection.

The reaction of the 3(4), 8(9)-bis(hydroxymethyl)tricyclo[5.2.1.0$^{2,6}$]decanes with isocyanates to form the corresponding urethanes is likewise known. Thus DE 35 22 006 A1 describes the reaction of the 3(4), 8(9)-bis(hydroxymethyl)tricyclo[5.2.1.0$^{2,6}$]decane with 2-isocyanatoethyl methacrylate. 2-isocyanatoethyl methacrylate is commercially available or can be synthesized according to the preparation specification from DE 33 38 077 A1 by phosgenation of dihydrooxazines.

The reaction product obtained (Formula (1)) of 2-isocyanatoethyl methacrylate with 3(4), 8(9)-bis(hydroxymethyl)tricyclo[5.2.1.0$^{2,6}$]decane in a formulation following curing has a lower reaction shrinkage and a high mechanical strength.

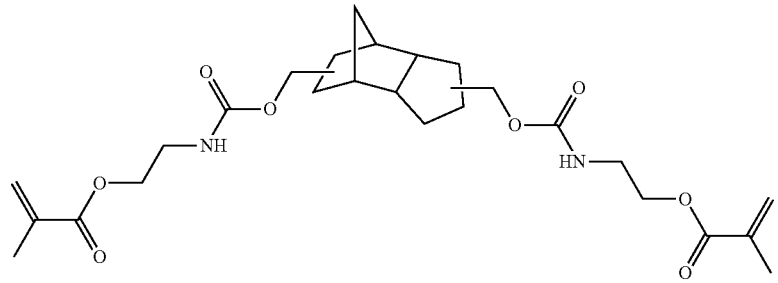

Formula (1)

The urethane of Formula (1) still has two hydrogen atoms capable of reacting with nitrogen, which now in a second reaction stage are further reacted with excess isocyanate to form a compound according to the invention. In the process the allophanate of Formula (2) initially forms as a tetrafunctionalized radically cross-linkable compound. In turn this monomer also still has hydrogen atoms capable of reacting with nitrogen, which according to the invention when reacting with further isocyanate form the hexafunctionalized, radically curable allophanate of Formula (3).
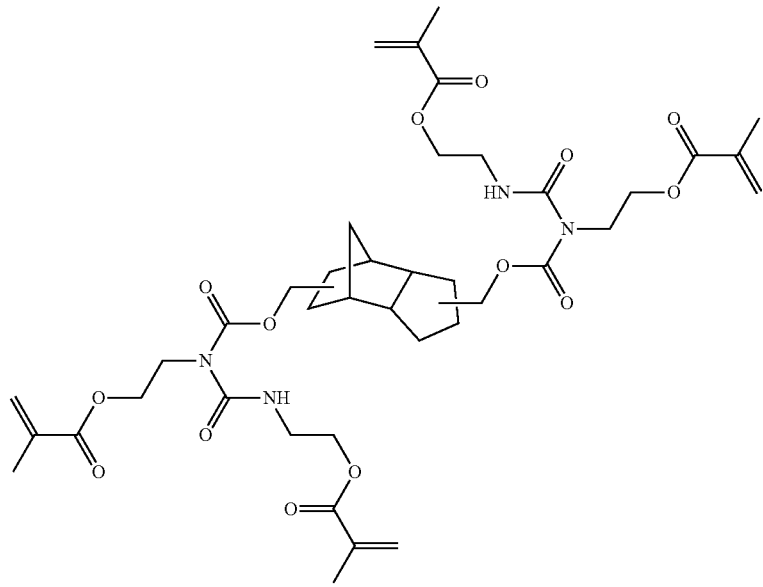
Formula (2)
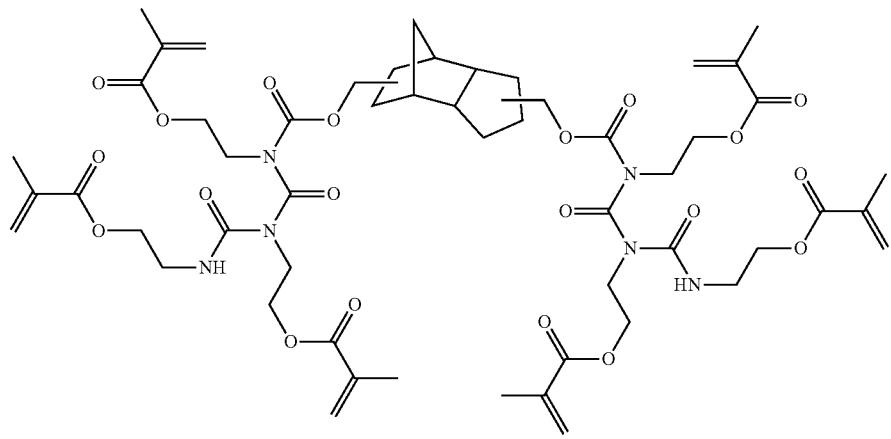
Formula (3)

Alternatively the 3(4), 8(9)-bis(hydroxymethyl)tricyclo[5.2.1.0$^{2,6}$]decane can also be brought into a reaction with methacryloyl isocyanate. Methacryloyl isocyanate is commercially available or can be obtained by reacting methacrylamide with oxalyl chloride, as described in EP 0 143 613 81. Through the reaction of 3(4), 8(9)-bis(hydroxymethyl)tricyclo[5.2.1.0$^{2,6}$]decane with methacryloyl isocyanate a compound of Formula (4) is obtained:

Formula (4)

The remaining hydrogen atoms able to react with nitrogen of the compound of Formula (4) can then in turn be reacted in isocyanate reactions to form allophanates. The reaction product with 2-isocyanatoethyl methacrylate (Formula (5)) is shown here as an example.

Formula (5)

2.) Starting with 3(4), 8(9)-bis(carboxylic acid)tricyclo[5.2.1.0$^{2,6}$]decane The 3(4), 8(9)-bis(carboxylic acid)tricyclo[5.2.1.0$^{2,6}$]decane is preparable by simple oxidation of the commercially available 3(4), 8(9)-bis(formyl)tricyclo[5.2.1.0$^{2,6}$]decane. Reaction of the dicarboxylic acid with 2-isocyanatoethyl methacrylate produces the amide of Formula (8):

Formula (8)

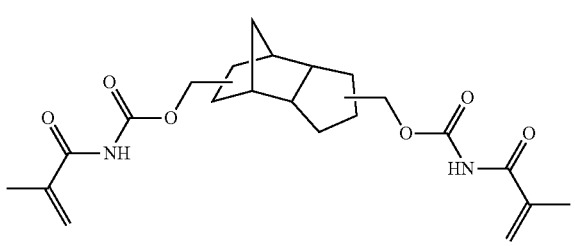

Further reaction of the two amide-hydrogen atoms of the amide of Formula (8) capable of reacting with 2-isocyanatoethyl methacrylate produces the acyl urea of Formula (9).

Formula (9)

If 3(4), 8(9)-bis(carboxylic acid)tricyclo[5.2.1.0$^{2,6}$]decane is reacted with methacryloyl isocyanate, the imide of Formula (10) results. The hydrogen atoms that react with nitrogen can here also be further reacted in isocyanate reactions.

Formula (10)

3.) Starting with 3(4), 8(9)-bis(isocyanatomethyl)tricyclo[5.2.1.0$^{2,6}$]decane The 3(4), 8(9)-bis(isocyanatomethyl)tricyclo[5.2.1.0$^{2,6}$]decane is in itself known and is one of the diisocyanate compounds commonly used in industrial applications (see DE 37 03 120 A1 and WO 2009/065873 A2). The conducting according to the invention of the second reaction stage of the isocyanate-alcohol reaction can be initiated not only starting with tricyclodecandiol and the isocyanatoethyl methacrylate, but also starting with the tricyclodecane diisocyanate and hydroxyethyl methacrylate. Through stoichiometric reaction of the two reactants the urethane of Formula (11) is obtained.

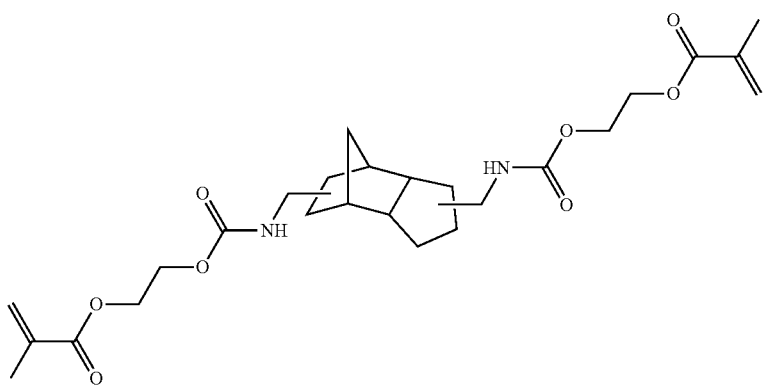

Formula (11)

This carbamate (Formula (11)) also has two hydrogen atoms capable of reacting with nitrogen, which can be further reacted with an excess of bis(isocyanatomethyl)tricyclo[5.2.1.0$^{2,6}$]decane to form the diisocyanate of Formula (12).

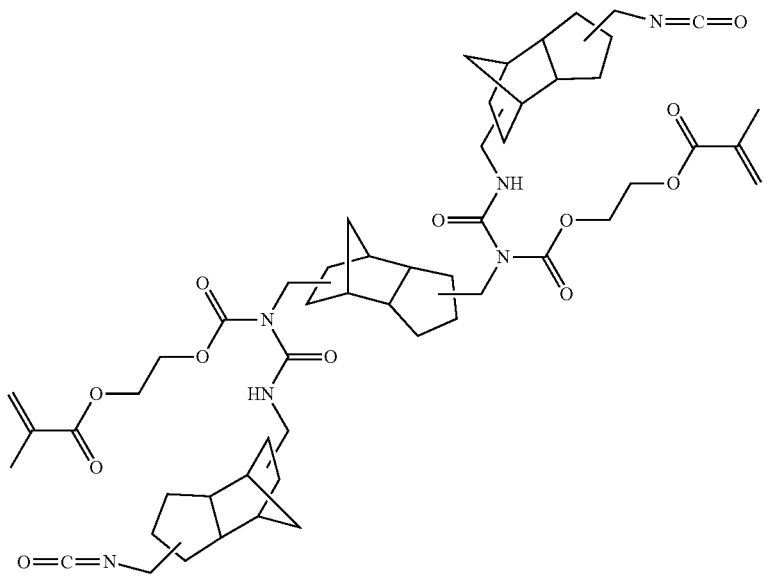

Formula (12)

Reaction of the allophanate diisocyanate (Formula 12) with methacrylic acid produces the compound of Formula (13).

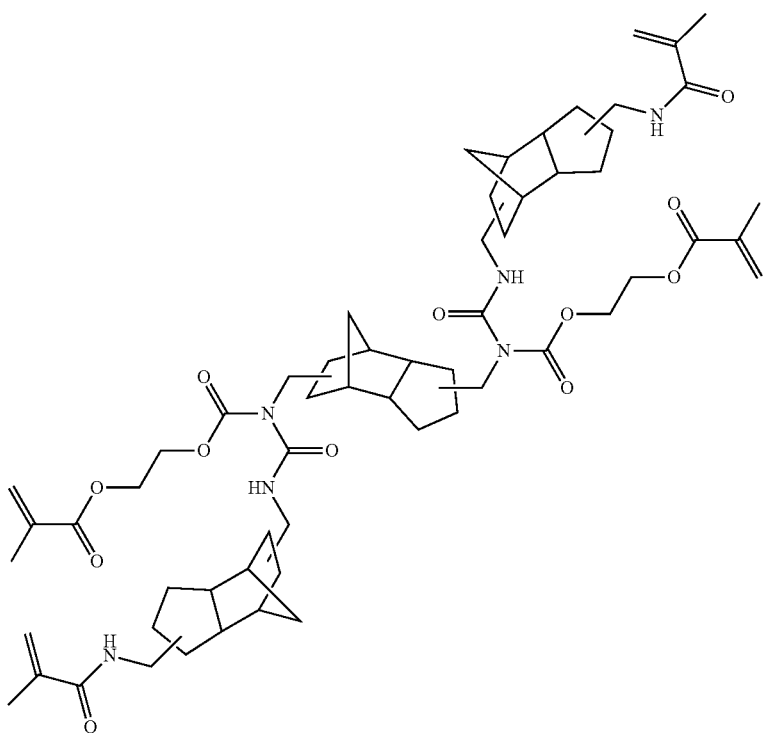

Formula (13)

Instead of hydroxyethyl methacrylate in the reactions described by way of example above other hydroxyl compounds of (meth)acrylates can be used, wherein mixtures of acrylates and methacrylates can also be used. So—analogously to the above example—3(4), 8(9)-bis(isocyanatomethyl)tricyclo[5.2.1.0$^{2,6}$]decane can be reacted. Here, preferred hydroxyl compounds of (meth)acrylates are those expressly mentioned above.

These compounds have both (meth)acrylate groups and hydroxy groups. The latter can react with isocyanate groups in the manner described above for the reaction between hydroxyethyl methacrylate and 3(4), 8(9)-bis(isocyanatomethyl)-tricyclo[5.2.1.0$^{2,6}$]decane. Thus in a single reaction step a high degree of functionalization can be achieved.

3(4), 8(9)-bis(isocyanatomethyl)tricyclo[5.2.1.0$^{2,6}$]decane can be reacted with 2-carboxylic acid-methacrylate to form the corresponding amide of Formula (16).

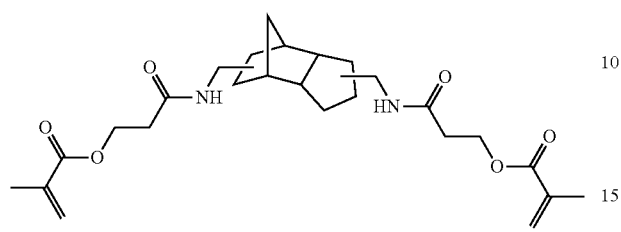

Formula (16)

Reacting of the amide of Formula (16) with 2-isocyanato-ethyl methacrylate produces the acyl urea of Formula (17).

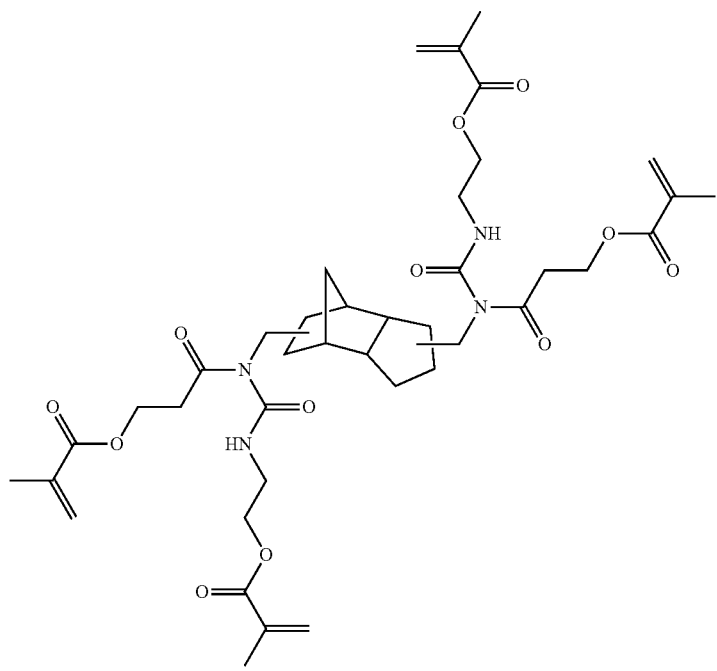

Formula (17)

The amide of Formula (16) can also be reacted with an excess of 3(4), 8(9)-bis(isocyanatomethyl)tricyclo[$5.2.1.0^{2,6}$]decane to form the corresponding isocyanate, wherein the isocyanate so formed is further reacted with hydroxyethyl methacrylate to form the cross-linkable monomer of Formula (18).

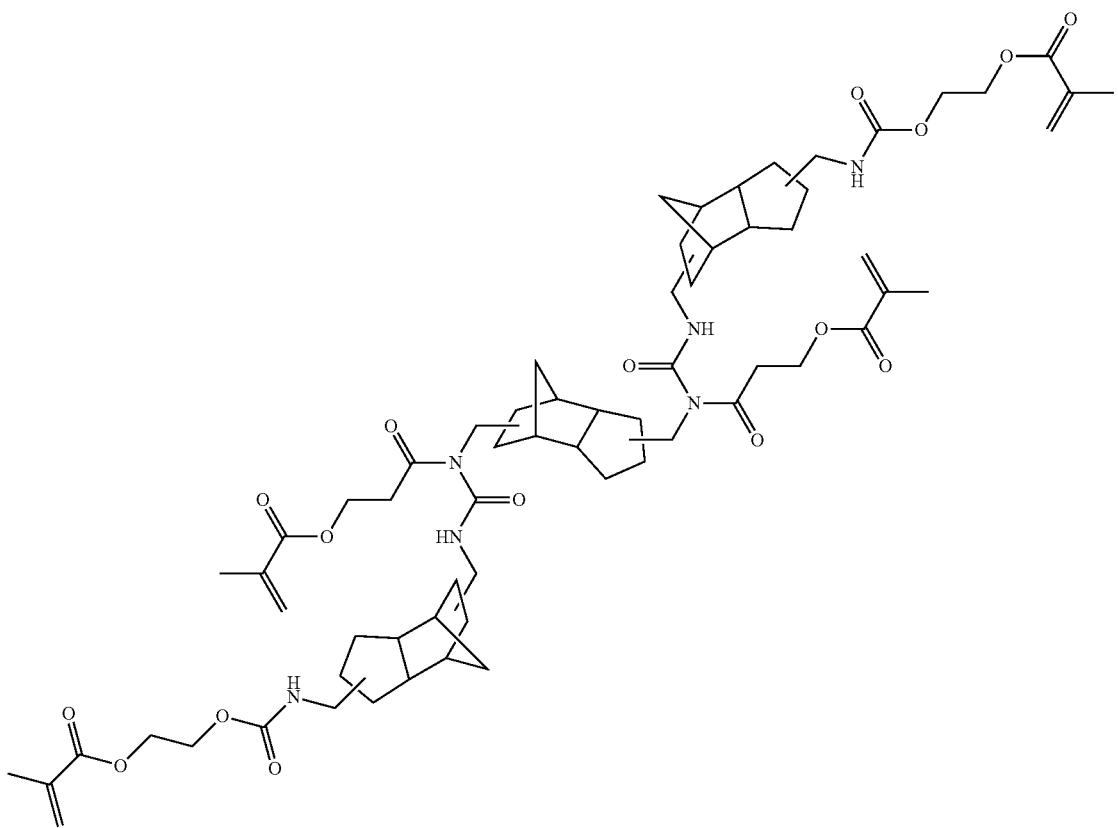
Formula (18)
If 3(4), 8(9)-bis(isocyanatomethyl)tricyclo[5.2.1.0$^{2,6}$]decane is reacted with 2-methacryloyloxy ethyl hydrogen succinate, then the amide of Formula (19) is obtained, which is further reacted with 2-isocyanatoethyl methacrylate to form the acyl urea of Formula (20).
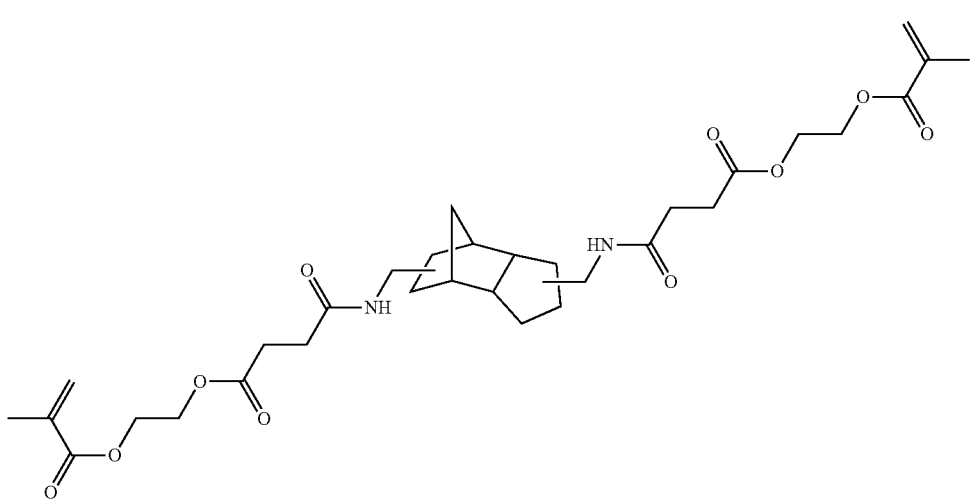
Formula (19)

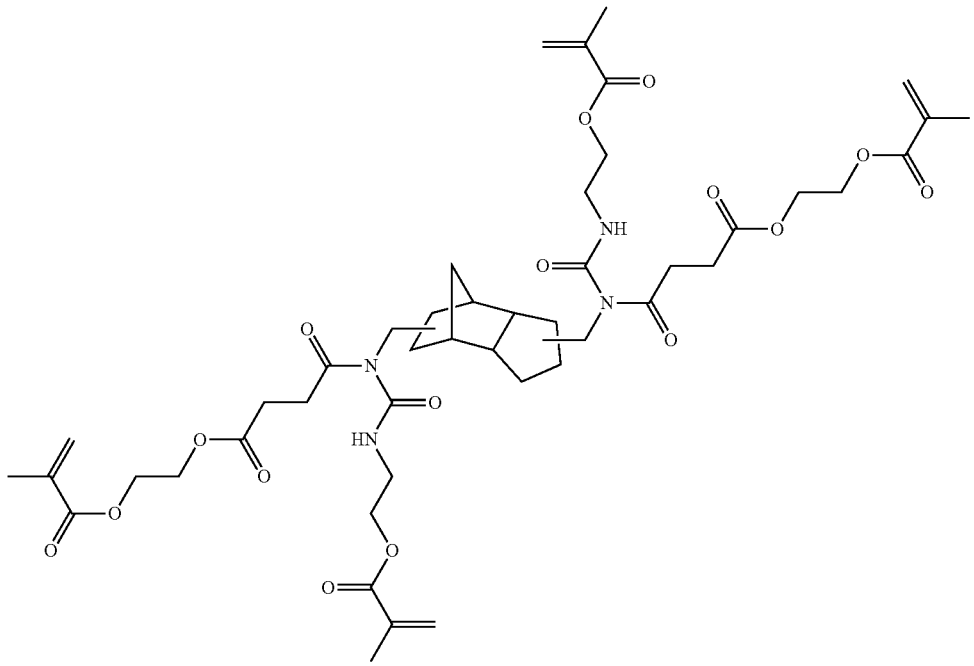

Formula (20)

Further suitable carboxylic acid methacrylates can be obtained from reactions between di- or tetracarboxylic acid mono- or dianhydride with suitable OH-functionalized, curable compounds such as for example 2-hydroxyethyl methacrylate.

4.) Starting with 3(4), 8(9)-bis(aminomethyl)tricyclo[5.2.1.0$^{2,6}$]decane

The 3(4), 8(9)-bis(aminomethyl)tricyclo[5.2.1.0$^{2,6}$]decane is in itself known or can be prepared for example by reaction of the corresponding tosylates with ammonia. Reaction of the 3(4), 8(9)-bis(aminomethyl)tricyclo[5.2.1.0$^{2,6}$]decane with 2-isocyanatoethyl methacrylate results in the urea compound of Formula (26) known from EP 0209700 A2.

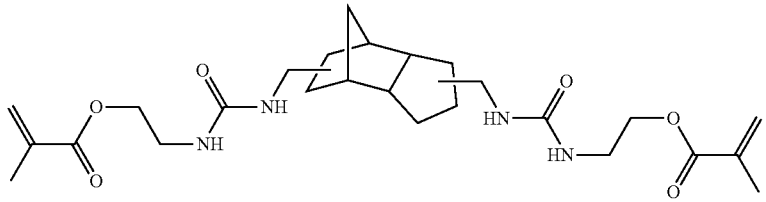

Formula (26)

Here again, there are still active hydrogen atoms capable of reacting with nitrogen which for example with an excess of isocyanate react to form the biuret of Formula (27).

Formula (27)

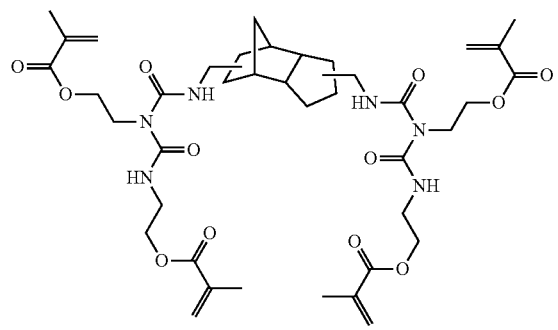

The 3(4), 8(9)-bis(aminomethyl)tricyclo[5.2.1.0$^{2,6}$]decane can also be brought into a reaction with methacryloyl isocyanate to form the corresponding acyl urea. The further reaction of the remaining hydrogen atoms reactive to nitrogen with methacryloyl isocyanate provides the biuret of Formula (28).

Formula (28)

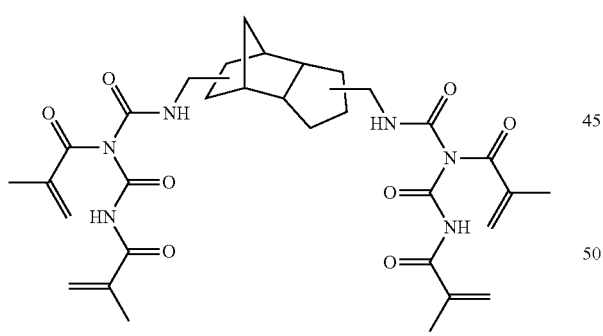

By analogy to the monomers described above, which comprise a polyalicyclic structure element Q derived from the tricyclo[5.2.1.0$^{2,6}$]decane, monomers can also be prepared, which comprise a polyalicyclic structure element Q derived from a tricyclo[3.3.1.1$^{3,7}$]decane (adamantane). The following reaction products are shown by way of examples:

Formula (29)

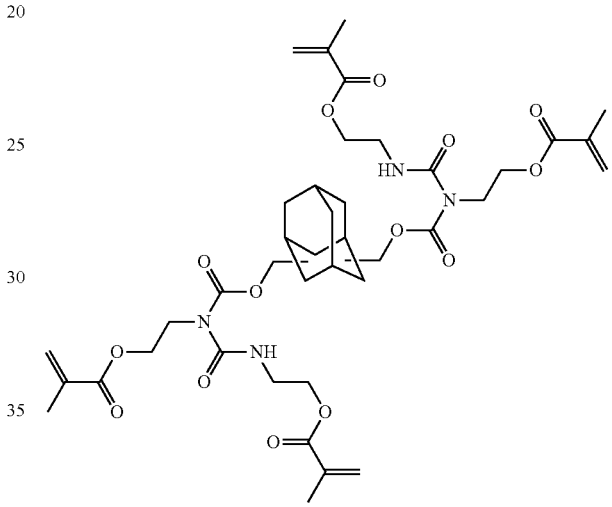

The reaction of the compound of Formula (11) with diisocyanatoadamantane [(bis(isocyanatomethyl)tricyclo[3.3.1.1$^{3,7}$]decane] provides a monomer according to the invention, the molecule of which comprises two polyalicylic structure elements that differ from one another, as shown in the following graphic formula of the compound of Formula (69).

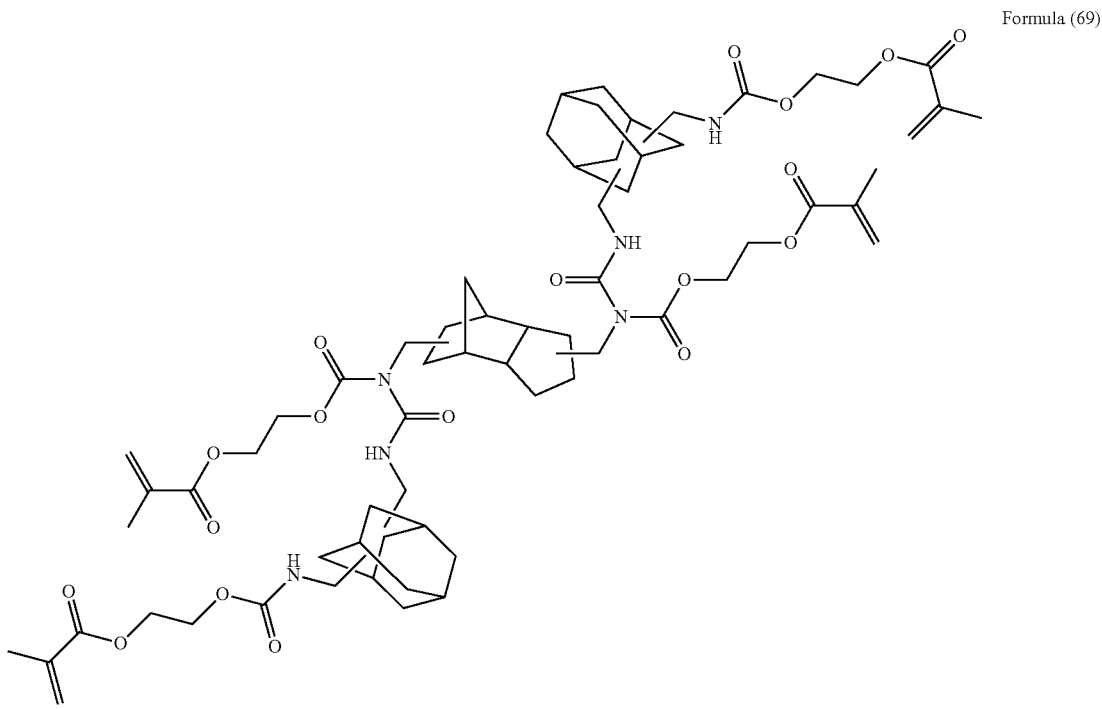

Formula (69)

Component (B2): One, Two or a Plurality of Further Radically Polymerizable Monomers from the Group Consisting of Acrylates and Methacrylates, Preferably from the Group of Methacrylates, The second constituent, that does not count as a component (b1), of the matrix-forming mixture of monomers is made up of radically polymerizable monomers selected from the group consisting of acrylates and methacrylates. Their function within the composite material according to the invention is substantially to adjust the viscosity.

According to the invention methacrylic acid esters or diesters are preferred because of their high biocompatibility compared with the corresponding acrylic acid esters or diesters.

The radically polymerizable monomers of component (b2) preferably have at least two ethylenic groups.

In the patent literature a number of diacrylate and dimethacrylate monomers are mentioned (for example also in DE 39 41 629 A1, which by way of reference is a constituent of this application, in particular the disclosure between column 6, line 15 and column 8, line 10), which are suitable for use in a composite material according to the invention.

In a preferred composite material according to the invention component (b2) contains one or a plurality of dimethacrylate monomers selected from the group consisting of ethylene glycol dimethacrylate (EGDMA), 1,6-hexanediol dimethacrylate (HEDMA), triethylene glycol dimethacrylate (TEDMA), 1,12-dodecandiol dimethacrylate (DODMA), ethoxylated bisphenol A dimethacrylate, polyethylene glycol dimethacrylate (PEGDMA), 7,7,9-trimethyl-4,13-dioxo-5,12-diazahexadecane-1,16-dioxydimethacrylate (UDMA), butanediol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol dimethacrylate, and glycerin dimethacrylate.

While bisphenol-A-glycidyl-methacrylate (Bis-GMA) can indeed be used, preferably a composite material according to the invention, in particular a dental composite material according to the invention, does not contain the compound Bis-GMA, however. Preferably a composite material according to the invention, in particular a dental composite material according to the invention, is free from all compounds with a bisphenol-A structure element.

The racially polymerizable monomers of component (b2) which are thus not part of component (b1) can also be hydroxyl compounds. Here all hydroxyl compounds of acrylates and methacrylates normally used in dental chemistry can be used. Preference is for hydroxyl compounds of methacrylates, and here in turn preference is for 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl-1,3-dimethacrylate, 3-hydroxypropyl-1,2-dimethacrylate, pentaerythritol dimethacrylate, glycerin dimethacrylate, and 2,2-bis[4-[3-methacryloyloxy-2-hydroxypropoxy]phenyl]propane.

As a further constituent photocurable acrylate or methacrylate monomers based on polysiloxanes, as for example described in DE 19903177 or in DE 4416857, which by way of reference are a constituent of this application, can also be used.

A composite material according to the invention, in particular a dental composite material according to the invention, can further in component (b2) contain one or a plurality of acid group-containing acrylate and/or methacrylate monomers. Such acid group-containing monomers can preferably have a carboxylic acid, a phosphoric acid, a phosphonic acid, a sulfonic acid and/or a thiophosphoric acid function. The monomer can contain one or a large number of acid functions in a molecule.

Suitable monomers containing a phosphoric acid group are, for example, 2-(meth)acryloyloxyethyl dihydrogen phosphate, bis[2-(meth)acryloyloxyethyl]hydrogen phosphate, 2-(meth)acryloyloxyethylphenyl hydrogen phosphate, 6-(meth)-acryloyloxyhexyl dihydrogen phosphate, 10-(meth)acryloyloxydecyl dihydrogen phosphate (MDP), 6-(meth)-acryloyloxyhexylphenyl hydrogen phosphate, 10-(meth)acryloyloxydecyl dihydrogen phosphate, 1,3-di-(meth)acryloyloxypropane-2-dihydrogen phosphate, 1,3-di-(meth)acryloyloxypropane-2-phenyl hydrogen phosphate and bis[5-(2-(meth)acryloyloxyethoxycarbonyl)heptyl]hydrogen phosphate.

Suitable monomers containing a carboxylic acid group are for example, 4-(meth)acryloxyethyl trimellith acid (4-MET), 4-(meth)acryloxyethyl trimellith acid anhydride (4-META), 4-(meth)acryloxydecyl trimellith acid, 4-(meth)acryloxydecyl trimellith acid anhydride, 11-(meth)acryloyloxy-1,1-undecane dicarboxylic acid, 1,4-di(meth)acryloyloxy pyromellith acid, 2-(meth)acryloyloxyethyl maleic acid, 2-(meth) acryloyloxyethyl phthalic acid and 2-(meth)acryloyloxyethyl hexahydrophthalic acid.

Other suitable acid group-containing monomers are mentioned in, for example, EP 0980682 B1 (in particular paragraphs [0059]-[0065]) or EP 0948955 (in particular paragraphs [0031]-[0034]), which by way of reference are a constituent of this application.

Further, phosphoric acid esters with glycerin dimethacrylate or with hydroxyethylmethacrylate or with hydroxypropylmethacrylate can also be used.

The monomers mentioned can be used individually or in mixtures.

Constituent (c): Initiators and/or Catalysts

A composite material according to the invention is preferably photocurable and/or chemically curable. Preference is for a composite material according to the invention, wherein constituent (c) comprises or consists of one or a plurality of photocuring initiators and/or one or a plurality of initiators for chemical curing.

Preferred composite materials according to the invention are photocurable and comprise photocuring initiators. Examples of a photoinitiator include substances which have solely a photo-sensitizing effect and combinations of sensitizers and accelerators.

Examples of photosensitizers are alpha-diketones, benzoin alkyl ethers, thioxanthones, benzophenones, acylphosphinoxides, acetophenones, ketals, titanocenes, sensitizing colorants, etc. The sensitizers can be used alone or in combination. Specific substance examples of the various classes can be found, for example, in DE 10 2006 019 092 A1 or in DE 39 41 629 C2, which by way of reference are a constituent of this application.

Examples of accelerators, which are used together with the sensitizers, are tertiary amines, secondary amines, barbituric acids, tin compounds, aldehydes and sulfur compounds. Specific substance examples of the various classes can be found in DE 10 2006 019 092 A1 or in DE 39 41 629 C2, which by way of reference are a constituent of this application.

Further suitable initiators and initiator combinations are described in DE 601 16 142, which by way of reference are a constituent of this application.

The photoinitiators used in connection with the present invention are characterized in that through the absorption of light in the wavelength range 300 nm through 700 nm, preferably 350 nm through 600 nm and particularly preferably 380 through 500 nm, optionally in combination with one or a plurality of co-initiators, they can bring about the curing of a composite material according to the invention, in particular a dental composite material according to the invention.

The absorption maximum of camphorquinone (CQ) is approximately 470 nm and thus in the range of blue light. Campherquinone (CQ) is one of the $PI_2$-initiators and is regularly used together with a co-initiator.

A composite material according to the invention preferably contains a combination of an alpha-diketone and an aromatic tertiary amine, preferably the combination is of camphorquinone (CQ) and ethyl-p-N,N-dimethylaminobenzoate (DABE).

Likewise preferred is the further combination of the "alpha-diketone/aromatic tertiary amine" system with a phosphine oxide, in particular with phenyl-bis(2,4,6-trimethylbenzoyl)phosphine oxide and/or 2,4,6-trimethylbenzoyl-diphenyl phosphine oxide. Regarding the structures of suitable phosphine oxides for use in a composite material according to the invention reference is made to printed publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2, which by way of reference are a constituent of this application.

The phosphine oxides indicated in these printed publications are particularly suitable on their own or in combination with the "alpha-diketone/amine" system as a photopolymerization initiator system in a composite material according to the invention.

Alternatively borate salts, as described for example in U.S. Pat. No. 4,772,530, U.S. Pat. No. 4,954,414, U.S. Pat. No. 4,874,450, U.S. Pat. No. 5,055,372 and U.S. Pat. No. 5,057,393, can be used as photoinitiators, which by way of reference are a constituent of this application.

Further suitable photoinitiators are described in J.-P. Fouassier, Photoinitiation, Photopolymerization and Photocuring, Hanser Publishers, Munich, Vienna, New York 1995 and in J. F. Rabek (publisher), Radiation Curing in Polymer Science and Technology, Vol. II, Elsevier Applied Science, London, New York 1993, which by way of reference are a constituent of this application.

Various initiators for a chemical curing will be known to a person skilled in the art. In this connection reference is made by way of example to EP 1 720 506.

Preferred initiators for chemical curing are benzoyl peroxide, lauroyl peroxide in particular dibenzoyl peroxide in combination with amines such as N,N-dimethyl-p-toluidine, N,N-dihydroxyethyl-p-toluidine and structurally related amines.

Here the peroxides and the amines are spread across two different components of the dental material. During the mixing of the amine-containing components (so-called base paste) with the peroxide-containing components (so-called initiator or catalyst paste) through the reaction of amine and peroxide (redox reaction) the radical reaction is initiated.

Dual-curing systems comprise a combination of photoinitiators and initiators for chemical curing.

By way of example, the base paste can also contain a photoinitiator, so that the base paste can be used either on its own as a photo-curing agent or together with the initiator paste as a photo- and self-curing dental material.

Apart from the organic peroxide compounds with an oxidative effect, barbituric acids or barbituric acid derivatives and malonyl sulfamides can also be used as redox systems.

Of the barbituric acid systems the so-called Bredereck systems are of great significance. Examples of suitable Bredereck systems and references to the corresponding patent literature can be found in EP 1 839 640 and in DE 14 95 520, WO 02/092021 or in WO 02/092023, which by way of reference are a constituent of this application.

Suitable malonyl sulfamides are described in EP 0 059 451 which by way of reference is a constituent of this application. Preferred compounds here are 2,6-dimethyl-4-isobutylmalonyl sulfamide, 2,6-diisobutyl-4-propylmalonyl sulfamide, 2,6-dibutyl-4-propylmalonyl sulfamide, 2,6-dimethyl-4-methylmalonyl sulfamide and 2. 6,6-dioctyl-4-isobutylmalonyl sulfamide.

Sulfur compounds in the oxidation stage +2 or +4 such as sodium benzene sulfinate or sodium paratoluene sulfinate can also be used.

In order to accelerate the curing the polymerization can be carried out in the presence of compounds of heavy metals such as Ce, Fe, Cu, Mn, Co, Sn or Zn, wherein copper compounds are particularly preferred. The heavy metal compounds are preferably used in the form of soluble organic compounds. Preferred copper compounds here are copper benzoate, copper acetate, copper ethyl hexanoate, copper di(methacrylate) and copper naphthenate.

Constituent (d): Optional Further Additives

A composite material according to the invention in some cases comprises one or a plurality of further additives.

These additives can have various functions. Normal additives for use in dental composite materials are known to a person skilled in the art who will select the appropriate additive(s) according to the desired function. In the following examples of typical additives and their functions are provided.

Photocurable dental composite materials, as preferred according to the invention, preferably contain one or a plurality of inhibitors, also referred to as stabilizers. These are normally added in order to prevent spontaneous polymerization. They react with prematurely forming radicals, which are intercepted, prevent premature polymerization and increase the storage stability of the photocurable dental composition. Common inhibitors are phenol derivates such as hydroquinone monomethylether (HQME) or 2,6-di-tert.butyl-4-methylphenol (BHT). Further inhibitors such as tert.-butylhydroxy anisol (BHA), 2,2 diphenyl-1-picrylhydrazyl, galvinoxyl, triphenylmethyl radicals, 2,3,6,6,-tetramethylpiperidinyl-1-oxyl radicals (TEMPO) and derivatives of TEMPO or phenothiazine and derivatives of this compound are described in EP 0 783 880 B1 which by way of reference are a constituent of this application. Alternative inhibitors are indicated in DE 101 19 831 A1 or in EP 1 563 821 A1, which by way of reference are a constituent of this application.

A dental composite material preferred according to the invention thus comprises as an additive one or a plurality of polymerization inhibitors to increase the storage stability of the composite material, preferably selected from the group consisting of hydroquinone monomethylether (HOME), phenols, here in preferably 2,6-di-tert.butyl-4-methyl phenol (BHT) and tert.-butylhydroxy anisol (BHA), 2,2-diphenyl-1-picrylhydrazyl radicals, galvinoxyl radicals, triphenylmethyl radicals, 2,3,6,6,-tetramethylpiperidinyl-1-oxyl radicals (TEMPO) and derivatives thereof and phenothiazine and derivatives thereof.

A dental composite material according to the invention can comprise as an additive one or a plurality of fluoride releasing substances, here preferably sodium fluoride and/or aminofluoride.

UV absorbers, which for example as a result of their conjugated double bonding systems and aromatic rings are capable of absorbing UV radiation, are in some cases a constituent of a composite material (preferably a dental composite material) according to the invention. Examples of UV absorbers are 2-hydroxy-4-methoxybenzophenone, salicylic acid phenyl ester, 3-(2'-hydroxy-5'-methylphenyl)-benzotriazole, or diethyl-2,5-dihydroxy-terephthalate.

Since the teeth are to be rebuilt to look as true to life as possible, it is necessary for the dental composite materials according to the invention to be provided in the most varied of color tones. To this end as a rule inorganic colorants and organic pigments in very small quantities are used, which in preferred configurations are thus used as an additive.

Further optional additives are aromatic substances.

The present invention also relates to a composite material according to the invention as a dental material or for use as a dental material, in particular as a restorative composite material, in particular as a filling, underfilling, securing and/or stump build-up material, as a temporary crown and/or bridge material, as a prosthesis and/or relining material or as a flow material.

The present invention also relates to a composite material according to the invention, in particular in one of the configurations identified as preferred or particularly preferred, for use in a therapeutic dental method as a dental material, particularly for filling, underfilling and securing of teeth and/or for building-up stumps, or for producing temporary crowns and/or bridges. The method can include providing the composite material as described herein and applying the composite material to tissue of a patient as part of a medical procedure, such as a dental procedure. The method can further include curing the composite material. As used herein, "tissue" is intended to have its conventional meaning and include all features of teeth.

The present invention also relates to the use of a composite material according to the invention for the production and/or lining of prostheses or for the preparation of a (preferably dental) flow material.

The present invention also relates to a product, obtainable by curing of a composite material according to the invention, in particular in one of the configurations identified as particularly preferred.

The present invention also relates to a method for treating a dental disease, characterized in that a composite material according to the invention, preferably in one of the configurations identified as preferred, is used as a filling, underfilling, securing and/or stump build-up material, as a temporary crown and/or bridge material, as a prosthesis and/or lining material or as a flow material.

The invention also relates to a method for preparation of a composite material according to the invention, in particular a dental composite material according to the invention, with the following step:

mixing of components (a), (b) and (c), and optionally (d).

The invention is further explained using the following examples.

EXAMPLES

The invention is further explained using the following examples. Unless otherwise indicated all data relate to the weight. The following abbreviations common in the trade are used here:

UDMA=urethane dimethacrylate (7,7,9-trimethyl-4,13-dioxo-5,12-diazahexadecane-1,16-dioxydimethacrylate)
TEDMA=triethylene glycol dimethacrylate
CQ=camphorquinone
DABE=ethyl-p-N,N-dimethylaminobenzoate
BHT=2,6-di-tert.butyl-4-methyl phenol
PPD=phenyl propandione Preparation of Composite Materials Composite materials according to the invention (Examples 1-10) and a comparative material (Example 11) not according to the invention, were prepared as follows:

The monomers (b1) and (b2), and initiators (c) and additives (d) are initially homogenized in a plastic container using a KPG stirrer. Then the fillers (a1), (a2) and optionally (a3) are added and through the thorough mixing of these with a dual-planet mixer a homogenous paste prepared.

The compositions of the composite materials (Example 1-10) according to the invention are given in Tables 1 and 2, and the composition of the composite material (comparative Example 11) not according to the invention in Table 3. The composition of components (c) and (d), in particular the selection of the UV absorber(s), where used, has no significant effect on the characteristics of the composite materials.

Measurement Methods:

Determination of the Average Particle Size:

The average particle sizes $d_{50}$ of the nanoparticles to be used according to the invention of component (a1) and the microparticles of component (a2) of the filler component of the dental composite material were determined with a Bechman Coulter LS 13320 particle size analyzer. To this end samples in each case with a weight of 50 mg were initially suspended for 5 minutes in 2 ml of isopropanol and then measured.

Determination of the Polymerization Shrinkage:

The polymerization volume shrinkage (polymerization shrinkage) was determined according to the bonded disc method (Dental Materials 2004, 20, 88-95). 100 mg of material were exposed for a period of 40 seconds (soft start) (Celalux2, VOCO GmbH Cuxhaven) and the polymerization shrinkage was measured over a period of 1,800 seconds.

Determination of the Abrasion (ACTA)

The three-media Acta Abrasion was determined according to the J. Dent. Suppl. 1, 1994, 22, 21-27 after 200,000 cycles.

Determination of the Vickers Microhardness

The Vickers microhardness was measured with an MTH 4 measuring device from Anton Paar (Graz, Austria) on 2×2 mm test specimens which had first been ground with 4000 grade grinding paper. Here the force was 1 N, the penetration speed 0.2 N/s and the dwell time 5 s.

Results

The results of the measurements of the polymerization shrinkage, of the Vickers microhardness and of the abrasion are shown for the composite materials according to the invention of Examples 1-10 in Tables 1 and 2 and for the composite material not according to the invention of Example 11 in Table 3.

All composite materials according to the invention (Examples 1-10) are characterized in the cured state by a low polymerization shrinkage (less than 1.7 vol. %, particularly preferred less than 1.6 vol. %), a low abrasion (less than 35 µm, particularly preferably less than 30 µm, determined according to the ACTA method) and a high Vickers microhardness (preferably 140 or more).

In the composite material not according to the invention of comparative Example 11 the amount of non-agglomerated, organically surface-modified nanoparticles with an average particle size of less than 200 nm is just 4.32 wt. %. This leads to an increase in the abrasion (37.2 µm), a reduction in the Vickers microhardness (123.7) and an increase in the polymerization shrinkage (2.13%), so that this composite material, unlike the composite materials according to the invention, is less suited to use in dentistry.

The compositions of the mixtures (in parts by weight) and the results of the measurements are listed in the Tables below.

TCD Monomers Used:

The TCD monomer of component (b1) used relates to in the Examples 1-4 and 6-9 according to the invention in each case bis(methacryloyloxymethyl)tricyclo[$5.2.1.0^{2,6}$]decane.

In Example 5 according to the invention, as in comparative example 11, bis(acryloyloxymethyl)tricyclo[$5.2.1.0^{2,6}$]decane was used as the TCD monomer.

In Example 10 according to the invention the compound of Formula (2) was used as the TCD monomer.

TABLE 1

| Example No | 1 | 2 | 3 | 4 | 5 |
|---|---|---|---|---|---|
| (a) Fillers | | | | | |
| (a1) SiO$_2$-nanopartiles ($d_{50}$ = 50 nm, silanized) | 22.82 | 22.81 | 22.81 | 23.44 | 22.62 |
| (a2) Microparticles, first fraction ($d_{50}$ = 1.5 µm, silanized dental glass) | 52.94 | 54.99 | 41.88 | 52.16 | 52.44 |
| (a2) Microparticles, second fraction ($d_{50}$ = 0.7 µm, silanized dental glass) | 14.07 | 12.04 | 25.15 | 13.95 | 14.86 |
| (b) Monomers | | | | | |
| (b1) TCD monomer | 7.67 | 5.75 | 4.79 | 1.97 | 7.60 |
| (b2) UDMA | 1.92 | 3.83 | 4.79 | 7.88 | 1.90 |
| (b2) TEDMA | 0.43 | 0.43 | 0.43 | 0.45 | 0.43 |
| (c) CQ | 0.05 | 0.05 | 0.05 | 0.05 | 0.05 |
| (c) DABE | 0.075 | 0.075 | 0.075 | 0.075 | 0.075 |
| (d) BHT | 0.015 | 0.015 | 0.015 | 0.015 | 0.014 |
| (d) UV-absorber | 0.072 | 0.072 | 0.072 | 0.074 | 0.071 |
| Weight ratio (b1/b2) | 3.26 | 1.35 | 0.92 | 0.24 | 3.26 |
| Vickers microhardness [MHV] | 157.5 | 147.2 | 156.3 | 168.7 | 160.3 |
| ACTA [µm] | 34.6 | 24.0 | 23.2 | 34.0 | 18.4 |
| Polymerization shrinkage [%] | 1.48 | 1.56 | 1.58 | 1.51 | 1.54 |
| Quotient (MHV/(ACTA * Polymerization shrinkage)) [100/µm] | 3.1 | 3.9 | 4.3 | 3.3 | 5.7 |

TABLE 2

| Example No | 6 | 7 | 8 | 9 | 10 |
|---|---|---|---|---|---|
| (a) Fillers | | | | | |
| (a1) SiO$_2$-nanopartiles ($d_{50}$ = 50 nm, silanized) | 22.79 | 22.51 | 22.52 | 24.19 | 22.62 |
| (a2) Microparticles, first fraction ($d_{50}$ = 1.5 µm, silanized dental glass) | 55.02 | 55.05 | 49.44 | 50.60 | 52.44 |
| (a2) Microparticles, second fraction ($d_{50}$ = 0.7 µm, silanized dental glass) | 12.03 | 12.52 | 17.97 | 14.41 | 14.86 |
| (b) Monomers | | | | | |
| (b1) TCD monomer | 3.59 | 6.31 | 4.73 | 0.51 | 7.60 |
| (b2) UDMA | 5.99 | 3.15 | 4.76 | 9.66 | 1.90 |
| (b2) TEDMA | 0.43 | 0.33 | 0.43 | 0.46 | 0.43 |
| (c) CQ | 0.05 | 0.04 | 0.05 | 0.06 | 0.05 |
| (c) DABE | 0.075 | 0.075 | 0.075 | 0.09 | 0.075 |
| (d) BHT | 0.015 | 0.014 | 0.014 | 0.016 | 0.014 |

TABLE 2-continued

| Example No | 6 | 7 | 8 | 9 | 10 |
|---|---|---|---|---|---|
| (d) UV-absorber | 0.072 | 0.07 | 0.071 | 0.076 | 0.071 |
| Weight ratio (b1/b2) | 0.56 | 1.81 | 0.91 | 0.05 | 3.26 |
| Vickers microhardness [MHV] | 153.8 | 142.2 | 140.4 | 139.8 | 162.5 |
| ACTA [µm] | 25.0 | 29.8 | 30.2 | 34.6 | 22.6 |
| Polymerization shrinkage [%] | 1.46 | 1.57 | 1.52 | 1.55 | 1.49 |
| Quotient (MHV/(ACTA * Polymerization shrinkage)) [100/µm] | 4.2 | 3.0 | 3.1 | 2.6 | 4.83 |

The following comparative example (Example 11) corresponds to representative composite materials from the prior art. This comparative example is based on Formulation 349 of EP 2016931 A2.

TABLE 3

| Example No | 11 (Comparative example) |
|---|---|
| (a) Fillers | |
| (a1) SiO$_2$-nanoparticles (d$_{50}$ = 50 µm, silanized) | 4.32 |
| (a2) Dental glass microparticles, first fraction (d$_{50}$ = 5.0 µm, silanized) | 39.38 |
| (a2) Dental glass microparticles, second fraction (d$_{50}$ = 0.85 µm, silanized) | 39.38 |
| (b) Monomers | |
| (b1) TCD-di-HEA | 11.34 |
| (b2) UDMA | 2.7 |
| (b2) TEDMA | 2.88 |
| (c) Initiators (CC, DABE, PPD) | 0.1 |
| (d) Additives (UV absorbers, TEMPO, BHT, pigments) | 0.26 |
| Weight ratio (b1/b2) | 2.03 |
| Vickers microhardness [MHV] | 123.7 |
| ACTA [µm] | 37.2 |
| Polymerization shrinkage [%] | 2.13 |
| Ratio (MHV/(ACTA * Polymerisazation shrinkage)) [100/µm] | 1.6 |

Synthesis of the Compound of Formula (2)

0.95 g (4.84 mmol) of 3(4), 8(9)-bis(hydroxymethyl) tricyclo[5.2.1.0$^{2,6}$]decane were dissolved in 10 ml of toluene and 0.04 g of BHT and 0.103 g of the catalyst solution (0.50 g dibutyltin(II)dilaurate dissolved in 9.50 g toluene) were added. Under agitation 3.00 g (19.34 mmol, 4 equivalents) of isocyanatoethyl methacrylate dissolved in 10 ml of toluene were dropped in. Once addition was complete the dropping funnel was replaced by a reflux condenser and the reaction mixture heated to 120° C. with the continuation of the reaction being monitored by IR spectroscopy. After 72 hours a further 0.102 g of catalyst solution was added and heating continued until no further isocyanate bands were detected. The solvent was removed using the rotary evaporator. The allophanate of formula (2) was obtained in a yield of 3.83 g (4.69 mmol, 97%) as a light yellowy oil.

Examples 1 through 9 were repeated exchanging the TCD monomers used there for the compound of formula (2); these further examples are referred to as Examples S1 through S9. All parameters determined in Examples 1 through 9 were also determined for Examples S1 through S9. The values of the parameters determined for Examples S1 through S9 are similar to those from Examples 1 through 9 and to some extent surpass these. This shows in addition to Example 10, that the compound of Formula (2), which is representative of the compounds according to the invention, is eminently suitable for use in composite materials according to the invention.

The invention claimed is:

1. A composite material comprising:
   (a) a total quantity of fillers in the range >75 through 95 wt. %, in relation to the total weight of the composite material wherein the total quantity of fillers is a mixture of fillers comprising
      (a1) a total quantity in the range >10 through 30 wt. % of non-agglomerated, organically surface-modified nanoparticles with an average particle size of less than 200 nm,
   and
      (a2) a total quantity in the range of 45 through <85 wt. % of microparticles with an average particle size in the range 0.4 µm through 10 µm and
      (a3) optionally further fillers,
      wherein the weight percentages given for components (a1) and (a2) relate to the total weight of the composite material,
   (b) a total quantity of polymerizable monomers in the range 3 through <25 wt. %, in relation to the total weight of the composite material, wherein the total quantity of polymerizable monomers is a mixture of monomers comprising
      (b1) one, two or a plurality of monomers selected from the group consisting of compounds (monomers) with the structure $Q(Y_xZ_e)_b$, wherein the following applies:
         Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $Y_xZ_e$ is or are substituted by alkyl groups, alkoxy groups, halogen atoms or trifluormethyl groups;
         b is an integer selected from the group of integers 1, 2, 3 and 4,
         each Z represents a structure element, which independently of any further structure elements Z is selected from the group consisting of

—O—(C=O)—CH=CH$_2$, —O—(C=O)—C(CH$_3$)=CH$_2$,

—(C=O)—CH=CH$_2$, —(C=O)—C(CH$_3$)=CH$_2$,

—CH=CH$_2$, —C(CH$_3$)=CH$_2$ and —O—CH=CH$_2$, each index e is an integer, which independently of any further indices e is selected from the group of integers 1, 2, 3 and 4,
         each index x independently of any other indices x represents 0 or 1,
         each Y in the structure $Q(Y_xZ_e)_b$ where x=1 represents a structure element, which bonds the polyalicyclic structure element Q with e structure elements Z, wherein each Y is selected independently of any further structure elements Y,
      (b2) one, two or a plurality of further radically polymerizable monomers from the group consisting of acrylates and methacrylates,
      wherein the further radically polymerizable monomer(s) is/are not compounds (monomers) of the structure $Q(Y_xZ_e)_b$ defined above and
      wherein the ratio of the weight of component (b1) to the weight of component (b2) is in the range 1:20 through 4:1, (c) one or a plurality of initiators and/or catalysts, and
(d) optionally one or a plurality of other additives, wherein at least one Y comprises a functional group selected from the group consisting of urethane, urea, N-acyl urea, allophanate, biuret and amide, wherein the amide function is not directly linked with an N atom, an O atom or a carbonyl group, wherein the x corresponding to said at least one Y is 1.

2. The composite material as claimed in claim 1, wherein component (a2) contains two or a plurality of microparticle fractions, wherein one or a plurality of first microparticle fractions in each case has/have an average particle size in the range 1 μm through 10 μm, and wherein one or a plurality of second microparticle fractions in each case has/have an average particle size in the range >0.4 μm through <1 μm.

3. The composite material as claimed in claim 2, wherein the ratio of the total weight of the first microparticle fractions to the total weight of the second microparticle fractions is in the range 1:1 through 10:1, and/or
the ratio of the average grain size of the or a first microparticle fraction to the average grain size of the or a second microparticle fraction of component (a2) is in the range 1.5:1 through 10:1.

4. The composite material as claimed in claim 2, wherein the ratio of the total weight of the first microparticle fractions to the total weight of the second microparticle fractions is in the range 1.5:1 through 5:1, and/or
the ratio of the average particle size of the or a first microparticle fraction to the average particle size of the or a second microparticle fraction of component (a2) is in the range 2:1 through 5:1.

5. The composite material as claimed in claim 1, wherein component (a2) contains two or a plurality of microparticle fractions, wherein one or a plurality of first microparticle fractions in each case has/have an average particle size in the range 1 μm through 5 μm, and wherein one or a plurality of second microparticle fractions in each case has/have an average particle size in the range 0.5 μm through 0.8 μm.

6. The composite material as claimed in claim 1, wherein at least part of the microparticles of component (a2) are organically surface-modified particles, and/or at least part of the microparticles of component (a2) are dental glass particles.

7. The composite material as claimed in claim 6, wherein said organically surface-modified particles comprise silanized particles, and/or
wherein the organically surface-modified dental glass particles comprise silanized dental glass particles.

8. The composite material as claimed in claim 1, comprising:
(a) a total quantity of fillers in the range >75 through 95 wt. %, in relation to the total weight of the composite material, wherein the total quantity of fillers is a mixture of fillers consisting of
(a1) a total quantity in the range >10 through 30 wt. % of non-agglomerated, organically surface-modified nanoparticles with an average particle size of less than 200 nm, wherein these nanoparticles are not dental glass particles and
(a2) a total quantity in the range of 45 through <85 wt. % of microparticles with an average particle size in the range 0.4 μm through 10 μm, wherein these microparticles are dental glass particles and
(a3) optionally further fillers, wherein the further fillers are neither non-agglomerated, organically surface-modified particles nor dental glass particles,
wherein the weight percentages given for components (a1) and (a2) relate to the total weight of the composite material.

9. The composite material as claimed in claim 1, wherein the composite material does not contain any Bis-GMA.

10. The composite material as claimed in claim 1, wherein the composite material does not contain any compound with a bisphenol-A structure element.

11. The composite material as claimed in claim 1, wherein the composite material in the cured state has a polymerization shrinkage of less than 1.7 vol. % measured according to the bonded disc method and/or
the ratio of the Vickers microhardness of the composite material to the product of the microabrasion of the composite material (measured using the ACTA method) and the polymerization shrinkage of the composite material is more than 2 [100/μm].

12. The composite material as claimed in claim 1, wherein the composite material in the cured state has a polymerization shrinkage of less than 1.6 vol. %, measured according to the bonded disc method and/or
the ratio of the Vickers microhardness of the composite material to the product of the microabrasion of the composite material (measured using the ACTA method) and the polymerization shrinkage of the composite material is more than 2.5 [100/μm].

13. The composite material as claimed in claim 1, wherein component (a1) comprises non-agglomerated, organically surface-modified particles selected from the group consisting of oxides and mixed oxides.

14. The composite material as claimed in claim 1, wherein component (a1) comprises non-agglomerated, organically surface-modified particles selected from the group consisting of oxides or mixed oxides of the elements silicon, titanium, yttrium, strontium, barium, zirconium, hafnium, niobium, tantalum, tungsten, bismuth, molybdenum, tin, zinc, ytterbium, lanthanum, cerium, aluminum and mixtures thereof.

15. The composite material as claimed in claim 1, wherein the structure element Q of the compounds of structure $Q(Y_x Z_e)_b$ of component (b1) represents a tricyclo[$5.2.1.0^{2,6}$]decane radical, a tricyclo[$5.2.1.0^{2,6}$]dec-3-ene radical, a tricyclo[$3.3.1.1^{3,7}$]decane radical or a bicyclo[2.2.1]heptane radical.

16. The composite material as claimed in claim 1, wherein one, two or a plurality of compounds of structure $Q(Y_x Z_e)_b$, have a tricyclo[$5.2.1.0^{2,6}$]-decane or tricyclo[$5.2.1.0^{2,6}$]-decene structure element and Z is selected from the group consisting of —O—(C=O)—CH=CH$_2$ and —O—(C=O)—C(CH$_3$)=CH$_2$.

17. The composite material as claimed in claim 16, wherein Z represents the group —O—(C=O)—C(CH$_3$)=CH$_2$.

18. The composite material as claimed in claim 1, wherein component (b1) comprises bis(methacrylolyoxymethyl)tricyclo[$5.2.1.0^{2,6}$]decane and/or bis(acrylolyoxymethyl)tricyclo[$5.2.1.0^{2,6}$]decane.

19. The composite material as claimed in claim 1, wherein the composite material is photocurable and/or chemically curable.

20. The composite material as claimed in claim 1, wherein component (c) comprises one or a plurality of photocuring initiators and/or one or a plurality of initiators for chemical curing or consists of these initiators.

21. A product obtainable by curing a composite material as claimed in claim 1.

22. A method of performing a dental procedure, comprising:
applying a composite material according to claim 1 to tissue of a patient.

23. The method of performing a dental procedure as claimed in claim 22, wherein said composite material is applied: to serve as filling or underfilling material; for securing teeth; for building up stumps; for producing temporary crowns and/or bridges; and combinations thereof.

* * * * *